United States Patent
Fujii et al.

(10) Patent No.: US 11,155,873 B2
(45) Date of Patent: Oct. 26, 2021

(54) METHOD FOR DETECTING VARIATION OF REFERENCE SEQUENCE IN TARGET NUCLEIC ACID REGION

(71) Applicant: EPIGENERON, INC., Tokyo (JP)

(72) Inventors: Hodaka Fujii, Tokyo (JP); Toshitsugu Fujita, Tokyo (JP)

(73) Assignee: EPIGENERON, INC., Tokyo (JP)

( * ) Notice: Subject to any disclaimer, the term of this patent is extended or adjusted under 35 U.S.C. 154(b) by 0 days.

(21) Appl. No.: 17/045,825

(22) PCT Filed: Apr. 19, 2019

(86) PCT No.: PCT/JP2019/016843
§ 371 (c)(1),
(2) Date: Oct. 7, 2020

(87) PCT Pub. No.: WO2019/203350
PCT Pub. Date: Oct. 24, 2019

(65) Prior Publication Data
US 2021/0147940 A1    May 20, 2021

(30) Foreign Application Priority Data

Apr. 20, 2018  (JP) .............................. JP2018-081752

(51) Int. Cl.
C12Q 1/68       (2018.01)
C12Q 1/6883   (2018.01)
(Continued)

(52) U.S. Cl.
CPC ........... *C12Q 1/6883* (2013.01); *C12Q 1/686* (2013.01); *C12Q 1/6848* (2013.01); *C12Q 2600/156* (2013.01)

(58) Field of Classification Search
None
See application file for complete search history.

(56) References Cited

U.S. PATENT DOCUMENTS

2006/0183142 A1    8/2006   Choi et al.

FOREIGN PATENT DOCUMENTS

| JP | 2016-49107 | 4/2016 |
| KR | 10-2006-0085111 | 7/2006 |

OTHER PUBLICATIONS

Tanigawa et al. (PLoS One, 2014, 9(11):e113345, p. 1-10, IDS reference) (Year: 2014).*

(Continued)

*Primary Examiner* — Stephanie K Mummert
(74) *Attorney, Agent, or Firm* — Wenderoth, Lind & Ponack, L.L.P.

(57) ABSTRACT

Provided is a method for detecting a variation of a reference sequence in a target nucleic acid region,
the method comprising the steps of:
performing a template-dependent nucleic acid amplification reaction for amplifying a region containing the reference sequence using, as a template, a nucleic acid containing the target nucleic acid region, in the presence of a 10 to 200 nucleotide single-stranded nucleic acid capable of hybridizing with the reference sequence in the target nucleic acid region, and
examining the presence or absence of an amplified product,
wherein the single-stranded nucleic acid is RNA or a chimeric nucleic acid composed of RNA and one or more different nucleic acids,
wherein the single-stranded nucleic acid contains a sequence complementary to the reference sequence, and (Continued)

wherein the single-stranded nucleic acid has a higher complementarity to the reference sequence than to a variant sequence having a variation of the reference sequence.

14 Claims, 14 Drawing Sheets

Specification includes a Sequence Listing.

(51) Int. Cl.
   *C12Q 1/6848*   (2018.01)
   *C12Q 1/686*    (2018.01)

(56) References Cited

OTHER PUBLICATIONS

Fujita et al. (PLoS One, 2016, 11(4):e0153901, p. 1-17) (Year: 2016).*
English Translation of International Preliminary Report on Patentability dated Oct. 20, 2020 in International (PCT) Application No. PCT/JP2019/016843.
Fujita, Toshitsugu et al., "Detection of genome-edited cells using ORNi-PCR", Department of Biochemishy and Genome Biology, Hirosaki University Graduate School of Medicine, Nov. 29, 2018.
International Search Report (ISR) dated Jul. 23, 2019 in International (PCT) Application No. PCT/JP2019/016843.
Naoki Tanigawa et al., "Oligoribonucleotide (ORN) Interference-PCR (ORNi-PCR): A Simple Method for Suppressing PCR Amplification of Specific DNA Sequences Using ORNs", PLOS ONE. vol. 9, Issue 11, pp. 1-10, Nov. 2014, cited in CA.
Toshitsugu Fujita et al., "Detection of genome-edited cells by oligoribonucleotide interference-PCR", DNA Research, vol. 25, pp. 395-407, Apr. 27, 2018, cited in CA.
Toshitsugu Fujita et al., "A refined two-step oligoribonucleotide interference-PCR method for precise discrimination of nucleotide differences", Scientific Reports, vol. 8, pp. 1-16, Nov. 21, 2018, cited in CA.
Toshitsugu Fujita et al., "Detection of genome-edited cells using ORNi-PCT", On-line abstracts of the 41st annual meeting of the Molecular Biology Society of Japan, Nov. 9, 2018, cited in CA.
Jay Shendure et al., "The expanding scope of DNA sequencing", Nature Biotechnology, vol. 30, pp. 1084-1094, pp. 1-28, Nov. 2012, cited in the specification.
Takeshi Harayama et al., "Detection of genome-edited mutant clones by a simple competition-based PCR method", PLOS ONE, vol. 12, pp. 1-16, Jun. 6, 2017, cited in the specification.
Chuan Yu et al., "A PCR Based Protocol for Detecting Indel Mutations Induced by TALENs and CRISPR/Cas9 in Zebrafish", PLOS ONE, vol. 9, Issue 6, pp. 1-7, Jun. 2014, cited in the specification.
Yufeng Hua et al., "A simple and efficient method for CRISPR/Cas9-induced mutant screening", Journal of Genetics and Genomics, vol. 44, pp. 207-213, 2017, cited in the specification.
Ulrike Mock, et al., "mRNA transfection of a novel TAL effector nuclease (TALEN) facilitates efficient knockout of HIV co-receptor CCR5", Nucleic Acids Research, vol. 43, No. 11, pp. 5560-5571, May 11, 2015, cited in the specification.
Yuichiro Miyaoka et al., "Isolation of single-base genome-edited human iPS cells without antibiotic selection", Nat Methods, vol. 11, pp. 291-293, pp. 1-15, Sep. 2014, cited in the specification.
Scott D. Findlay et al., "A Digital PCR-Based Method for Efficient and Highly Specific Screening of Genome Edited Cells", PLOS ONE, vol. 11, pp. 1-17, Apr. 18, 2016, cited in the specification.
Xiaoxiao Zhu et al., "An Efficient Genotyping Method for Genome-modified Animals and Human Cells Generated with CRISPR/Cas9 System", Scientific Reports, vol. 4, pp. 1-8, 2014, cited in the specification.
Timothy J. Dahlem et al., "Simple Methods for Generating and Detecting Locus-Specific Mutations Induced with TALENs in the Zebrafish Genome", PLOS Genetics, vol. 8, Issue 8, pp. 1-15, August 2012, cited in the specification.
Zhang Yang et al., "Fast and sensitive detection of indels induced by precise gene targeting", Nucleic Acids Research, vol. 43, No. 9, pp. 1-8, Mar. 9, 2015, cited in the specification.
Muhammad Khairul Ramlee et al., "High-throughput genotyping of CRISPR/Cas9-mediated mutants using fluorescent PCR-capillary gel electrophoresis", Scientific Reports, vol. 5, pp. 1-13, 2015, cited in the specification.
Patrick L. Dominguez et al., "Wild-type blocking polymerase chain reaction for detection of single nucleotide minority mutations from clinical specimens", Oncogene (2005), vol. 24, pp. 6830-6834.

* cited by examiner

Fig. 10
(A)
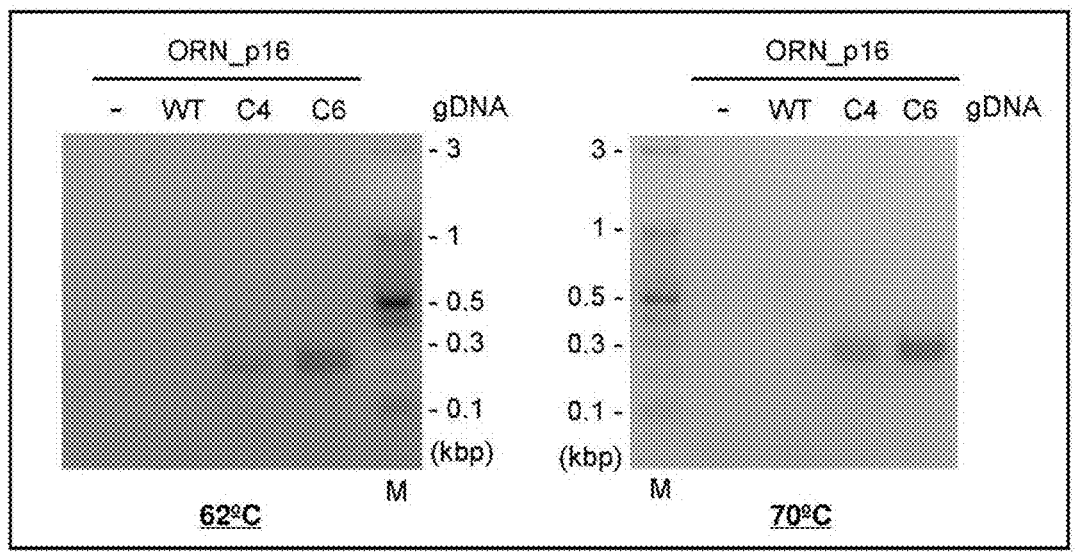
(B)
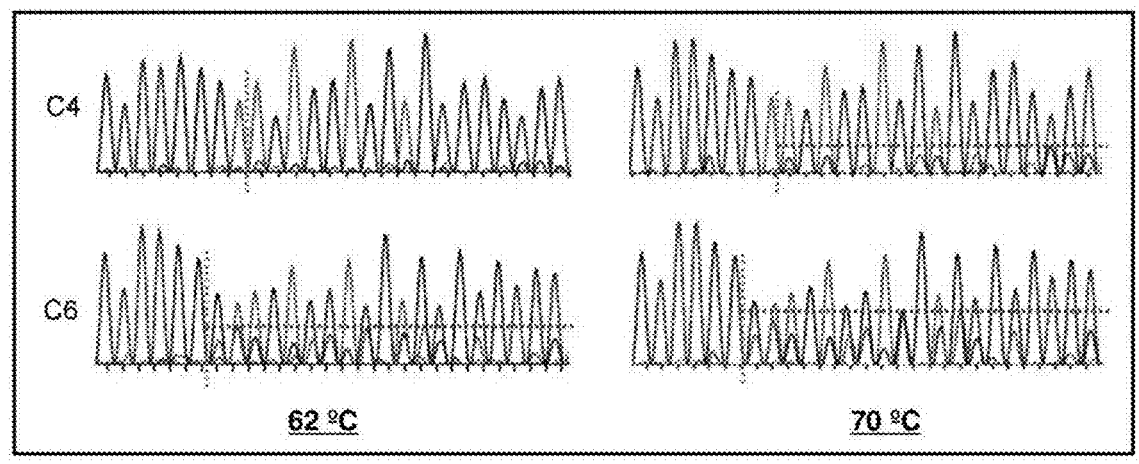

```
                        SEQUENCE LISTING

<160> NUMBER OF SEQ ID NOS: 58

<210> SEQ ID NO 1
<211> LENGTH: 20
<212> TYPE: RNA
<213> ORGANISM: Artificial Sequence
<220> FEATURE:
<223> OTHER INFORMATION: Oligo Ribonucleic Acid

<400> SEQUENCE: 1
cggggucucg acauggucac                                                     20

<210> SEQ ID NO 2
<211> LENGTH: 24
<212> TYPE: RNA
<213> ORGANISM: Artificial Sequence
<220> FEATURE:
<223> OTHER INFORMATION: Oligo Ribonucleic Acid

<400> SEQUENCE: 2 uccgggucu cgacaugguc acgc                                                 24

<210> SEQ ID NO 3
<211> LENGTH: 23
<212> TYPE: RNA
<213> ORGANISM: Artificial Sequence
<220> FEATURE:
<223> OTHER INFORMATION: Oligo Ribonucleic Acid

<400> SEQUENCE: 3
ccucuuccgg ggucucgaca ugg                                                 23

<210> SEQ ID NO 4
<211> LENGTH: 21
<212> TYPE: RNA
<213> ORGANISM: Artificial Sequence
<220> FEATURE:
<223> OTHER INFORMATION: Oligo Ribonucleic Acid

<400> SEQUENCE: 4
ccgggggcgc ugggcugucc c                                                   21

<210> SEQ ID NO 5
```

-continued

```
<211> LENGTH: 25
<212> TYPE: RNA
<213> ORGANISM: Artificial Sequence
<220> FEATURE:
<223> OTHER INFORMATION: Oligo Ribonucleic Acid

<400> SEQUENCE: 5
ggggccgggg gcgcugggcu guccc                                              25

<210> SEQ ID NO 6
<211> LENGTH: 21
<212> TYPE: RNA
<213> ORGANISM: Artificial Sequence
<220> FEATURE:
<223> OTHER INFORMATION: Oligo Ribonucleic Acid

<400> SEQUENCE: 6
caccuccucu acccgaccccc c                                                 21

<210> SEQ ID NO 7
<211> LENGTH: 20
<212> TYPE: RNA
<213> ORGANISM: Artificial Sequence
<220> FEATURE:
<223> OTHER INFORMATION: Oligo Ribonucleic Acid

<400> SEQUENCE: 7
gcggcccggg gucggguaga                                                    20

<210> SEQ ID NO 8
<211> LENGTH: 42
<212> TYPE: RNA
<213> ORGANISM: Artificial Sequence
<220> FEATURE:
<223> OTHER INFORMATION: Oligo Ribonucleic Acid

<400> SEQUENCE: 8
ccucuuccgg ggucucgaca guuuuagagc uaugcuguuu ug                           42

<210> SEQ ID NO 9
<211> LENGTH: 42
<212> TYPE: RNA
<213> ORGANISM: Artificial Sequence
<220> FEATURE:
<223> OTHER INFORMATION: Oligo Ribonucleic Acid

<400> SEQUENCE: 9
cggcaggcuc gggugcgccu guuuuagagc uaugcuguuu ug                           42

<210> SEQ ID NO 10
<211> LENGTH: 20
<212> TYPE: RNA
<213> ORGANISM: Artificial Sequence
<220> FEATURE:
<223> OTHER INFORMATION: Oligo Ribonucleic Acid

<400> SEQUENCE: 10
auauacggag uuaaggugua                                                    20

<210> SEQ ID NO 11
<211> LENGTH: 20
<212> TYPE: RNA
<213> ORGANISM: Artificial Sequence
<220> FEATURE:
<223> OTHER INFORMATION: Oligo Ribonucleic Acid

<400> SEQUENCE: 11
```
gcgccgcagc cacugcuuuu                                                20

<210> SEQ ID NO 12
<211> LENGTH: 21
<212> TYPE: RNA
<213> ORGANISM: Artificial Sequence
<220> FEATURE:
<223> OTHER INFORMATION: Oligo Ribonucleic Acid

<400> SEQUENCE: 12
caguuuggcc agcccaaaau c                                              21

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
agccagcaaa ttacttcatc atc                                            23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctcctcctcc atccacttag aat                                            23

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
ctgcagcgtg accatgtc                                                  18

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
cacccaacaa aagtgtctct gtg                                            23

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gttctcaaaa agcagggagt gaa                                            23

<210> SEQ ID NO 18
<211> LENGTH: 26
<212> TYPE: DNA

```
<213> ORGANISM: Artificial Sequence
<220> FEATURE:
<223> OTHER INFORMATION: Primer

<400> SEQUENCE: 18
ccgcagtcga gtctgcagag tgttgg                                          26

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
caaggctggg ctcaaattcc acatcc                                          26

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cggggtctcg acatggtcac                                                 20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gaggggctgg ctggtcacca ga                                              22

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
tgcagaccct ctacccacct ggat                                            24

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ccccgattca atttggcagt tagga                                           25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
attacaaacc ccttctgaaa actcc                                           25
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
actccatgct cctgccaaat                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ccagcgagct agccagagat                                                  20

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
ccgaagagtc tccaggctag aag                                              23

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
acctccttct gcacacattt gaa                                              23

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
ttgactgagt tgtatcccca tcc                                              23

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
tgcacagtgt ttagtatttc atggtg                                           26

<210> SEQ ID NO 31
<211> LENGTH: 25
<212> TYPE: DNA
<213> ORGANISM: Artificial Sequence
<220> FEATURE:

```
<223> OTHER INFORMATION: Primer

<400> SEQUENCE: 31
aactgtcttc agtttccgta caagg                                         25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
gggtgagtgg tagtaagaga ggcta                                         25

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
gcctttccat tctttggatc ag                                            22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ctgcagggag agactgaaac ct                                            22

<210> SEQ ID NO 35
<211> LENGTH: 39
<212> TYPE: DNA
<213> ORGANISM: Homo sapiens

<400> SEQUENCE: 35
ctgcagcgtg accatgtcga ccccggaa gaggctggc                            39

<210> SEQ ID NO 36
<211> LENGTH: 52
<212> TYPE: DNA
<213> ORGANISM: Homo sapiens

<400> SEQUENCE: 36
gcactaaagt ccctgcagc gtgaccatgt cgagaccccg gaagaggctg gc            52

<210> SEQ ID NO 37
<211> LENGTH: 43
<212> TYPE: DNA
<213> ORGANISM: Homo sapiens

<400> SEQUENCE: 37
ctggccacgg ccgcggcccg ggtcgggta gaggaggtgc ggg                      43

<210> SEQ ID NO 38
<211> LENGTH: 43
<212> TYPE: DNA
<213> ORGANISM: Homo sapiens

<400> SEQUENCE: 38
```

```
ctggccacgg ccgcggcccg gggtcgggta gaggaggtgc ggg                43
```

<210> SEQ ID NO 39
<211> LENGTH: 36
<212> TYPE: DNA
<213> ORGANISM: Homo sapiens

<400> SEQUENCE: 39

```
ccgcggcccg ggggtcgggt agaggaggtg cgggcg                       36
```

<210> SEQ ID NO 40
<211> LENGTH: 35
<212> TYPE: DNA
<213> ORGANISM: Homo sapiens

<400> SEQUENCE: 40

```
ccgcggcccg gggtcgggta gaggaggtgc gggcg                        35
```

<210> SEQ ID NO 41
<211> LENGTH: 28
<212> TYPE: DNA
<213> ORGANISM: Mus musculus

<400> SEQUENCE: 41

```
ccattacacc ttaactccgt atatccat                                28
```

<210> SEQ ID NO 42
<211> LENGTH: 30
<212> TYPE: DNA
<213> ORGANISM: Homo sapiens

<400> SEQUENCE: 42

```
gttataaaag cagtggctgc ggcgcctcgt                              30
```

<210> SEQ ID NO 43
<211> LENGTH: 65
<212> TYPE: DNA
<213> ORGANISM: Homo sapiens

<400> SEQUENCE: 43

```
ctcattcata aaacgcttgt tataaaagca gtggctgcgg cgcctcgtac tccaaccgca    60
tctgc                                                              65
```

<210> SEQ ID NO 44
<211> LENGTH: 31
<212> TYPE: DNA
<213> ORGANISM: Homo sapiens

<400> SEQUENCE: 44

```
tcacagattt tgggctggcc aaactgctgg g                            31
```

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45

```
ggagacccaa cctggggcga cttca                                   25
```

<210> SEQ ID NO 46

```
<211> LENGTH: 25
<212> TYPE: DNA
<213> ORGANISM: Artificial Sequence
<220> FEATURE:
<223> OTHER INFORMATION: Primer

<400> SEQUENCE: 46
ctgtacgcgc gtggctcctc attcc                                          25

<210> SEQ ID NO 47
<211> LENGTH: 40
<212> TYPE: RNA
<213> ORGANISM: Artificial Sequence
<220> FEATURE:
<223> OTHER INFORMATION: Oligo Ribonucleic Acid

<400> SEQUENCE: 47
uggggcggac cgcgugcgcu guuuuagagc uaugcuguuu                          40

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
tttttagagg atttgaggga tagg                                           24

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
ctacctaatt ccaattcccc tacaaacttc                                     30

<210> SEQ ID NO 50
<211> LENGTH: 23
<212> TYPE: RNA
<213> ORGANISM: Artificial Sequence
<220> FEATURE:
<223> OTHER INFORMATION: Oligo Ribonucleic Acid

<400> SEQUENCE: 50 gugggagua guauggaguu uuu                                             23

<210> SEQ ID NO 51
<211> LENGTH: 33
<212> TYPE: DNA
<213> ORGANISM: Homo sapiens

<400> SEQUENCE: 51
cagcgtgacc atgtcgagac cccggaagag gct                                 33

<210> SEQ ID NO 52
<211> LENGTH: 41
<212> TYPE: DNA
<213> ORGANISM: Homo sapiens

<400> SEQUENCE: 52
tgcagcgtga ccatgtcgag accccggaag aggctggctg g                        41
```

```
<210> SEQ ID NO 53
<211> LENGTH: 27
<212> TYPE: DNA
<213> ORGANISM: Homo sapiens

<400> SEQUENCE: 53
ggtggggcgg accgcgtgcg ctcggcg                                          27

<210> SEQ ID NO 54
<211> LENGTH: 34
<212> TYPE: DNA
<213> ORGANISM: Homo sapiens

<400> SEQUENCE: 54
ggtggggcgg accgcgtgcg ctcggcggct gcgg                                  34

<210> SEQ ID NO 55
<211> LENGTH: 392
<212> TYPE: DNA
<213> ORGANISM: Homo sapiens

<400> SEQUENCE: 55
cctccagagg atttgaggga cagggtcgga gggggctctt ccgccagcac cggaggaaga      60
aagaggaggg gctggctggt caccagaggg tgggcggac cgcgtgcgct cggcggctgc      120
ggagaggggg agagcaggca gcgggcggcg gggagcagca tggagccggc ggcggggagc     180
agcatggagc cttcggctga ctggctggcc acggccgcgg cccggggtcg ggtagaggag     240
gtgcgggcgc tgctggaggc gggggcgctg cccaacgcac cgaatagtta cggtcggagg     300
ccgatccagg tgggtagagg gtctgcagcg ggagcagggg atggcgggcg actctggagg     360
acgaagtttg cagggaatt ggaatcaggt ag                                    392

<210> SEQ ID NO 56
<211> LENGTH: 23
<212> TYPE: DNA
<213> ORGANISM: Artificial Sequence
<220> FEATURE:
<223> OTHER INFORMATION: DNA amplified using bisulfite-treated DNA as a
      template

<400> SEQUENCE: 56
aaaaactcca tactactccc cac                                              23

<210> SEQ ID NO 57
<211> LENGTH: 23
<212> TYPE: DNA
<213> ORGANISM: Artificial Sequence
<220> FEATURE:
<223> OTHER INFORMATION: DNA amplified using bisulfite-treated DNA as a
      template

<400> SEQUENCE: 57
gaaaactcca tactactccc cgc                                              23

<210> SEQ ID NO 58
<211> LENGTH: 21
<212> TYPE: DNA
<213> ORGANISM: Artificial Sequence
<220> FEATURE:
```

```
<223> OTHER INFORMATION: DNA amplified using bisulfite-treated DNA as a
      template

<400> SEQUENCE: 58
cggatcgcgt gcgttcggcg g                                                  21
```

METHOD FOR DETECTING VARIATION OF REFERENCE SEQUENCE IN TARGET NUCLEIC ACID REGION

TECHNICAL FIELD

The present invention relates to a method for detecting a variation of a reference sequence in a target nucleic acid region using a template-dependent nucleic acid amplification reaction.

BACKGROUND ART

Various methods for detecting a mutation (insertion, deletion, or substitution) of one or more nucleotides in DNA or RNA, that is, a variation of a reference sequence (e.g., wild-type sequence) have been reported as follows.

(1) Nucleotide Sequencing

In general, for detecting mutations, a nucleic acid to be analyzed is sequenced and compared with the wild-type sequence. Commonly used sequencing methods include Sanger sequencing (dideoxy method) and a series of next-generation sequencings (Non Patent Literature 1). Such a method can determine whether or not a sample to be analyzed has mutations and what kind of mutations the sample has. However, this approach requires nucleic acid extraction from cells, PCR amplification of the nucleic acid sequence of interest, and if necessary, cloning into plasmids etc. before sequencing, and thus is enormously time-consuming when applied to detection of genome-edited cells and of mutated cells in clinical samples. Therefore, nucleotide sequencing is not suitable at least for screening for mutated cells. There is a need for simpler methods for screening.

(2) PCR Method Using Primer for DNA Region that is Likely to be Mutated

Recent publications report a PCR method using a primer for a wild-type DNA region that is likely to be mutated and another primer which yields an amplified product in combination with the above primer (Non Patent Literature 2, 3, and 4). In this method, a PCR product is obtained from a wild-type DNA, but not a mutant DNA, and this feature is utilized for detecting a sample containing a mutant DNA. In this method, the absence of an amplified product, that is, a negative signal indicates the detection of a mutation. However, in consideration that there are many factors that may interfere with PCR reactions, this method has a high possibility that false-positive results occur. For accurate detection of a mutation, many samples need to be analyzed.

(3) PCR Method Using Fluorophore- and Quencher-Labeled Oligonucleotide Probe Such as TaqMan Probe For detecting a mutant DNA, a commonly used approach is to add, to a PCR reaction system, an oligonucleotide probe that is labeled with a fluorophore (at the 5' end of the probe) and a quencher (at the 3' end of the probe) and targets a DNA region that is likely to be mutated (Non Patent Literature 5 to 7). In this method, the probe anneals to a wild-type DNA template, which causes cleavage of the probe by the exonuclease activity of the DNA polymerase used for PCR. As a result, the fluorophore and the quencher are separated, and fluorescence occurs in the reaction system. In contrast, the probe does not anneal to a mutant DNA template, and fluorescence does not occur. For this analysis, a real-time PCR cycler or a digital PCR device for fluorescence detection is required. In addition, in the case where a sample contains a wild-type DNA and a mutant DNA, fluorescence occurs due to the presence of the wild-type DNA in the sample, which makes it difficult to use this method for detection of a heterozygous mutation.

(4) Surveyor Assay

In Surveyor assay, initially, a control DNA and a test DNA are amplified by PCR. These DNAs are mixed in a test tube and subjected to thermal denaturation and subsequent annealing. The annealed DNA is treated with surveyor nuclease to cleave at the 3' side of a mismatch base. Through this procedure, it can be determined whether the test DNA contains a base that is different from the corresponding one in the control DNA (Non Patent Literature 8). This method usually requires nucleic acid extraction from cells and PCR amplification of a nucleic acid sequence of interest in advance. This method is relatively simple and is mainly used to determine genome editing efficiency using a DNA extracted from genome-edited cell "population". In this case, a control DNA is not necessary because the genome editing efficiency usually does not reach 100%, and genome editing occurs in a various manner. However, for the detection of individual genome-edited cells, mixing with DNA of wild-type cells is needed because otherwise homozygous mutations cannot be detected. For the analysis of individual cells, the above-described nucleotide sequencing rather than surveyor assay is usually employed because it is a more direct method than surveyor assay.

(5) High Resolution Melting Analysis (HRMA)

This method detects a difference between nucleotide sequences by analysis of the melting curves of PCR products (Non Patent Literature 9). This analysis can easily be performed but requires an instrument for detecting a melting curve (real-time PCR cycler etc.).

(6) Capillary Electrophoresis

Capillary electrophoresis is performed on PCR products containing a mutated region, and their lengths are accurately measured, thereby detecting base indels (Non Patent Literature 10 and 11). However, this method is time-consuming and requires a capillary electrophoresis instrument. Further, this method is not suitable for detecting a variation of wild-type because the length of the PCR product remains unchanged in the case of substitution mutation of nucleotides.

The present inventors have developed and applied for a patent on a method for specifically inhibiting nucleic acid amplification of a target region in a reaction system containing a single-stranded nucleic acid capable of hybridizing with the target region (Patent Literature 1). However, Patent Literature 1 does not describe any method for detecting a mutation (variation of a reference sequence) in a target nucleic acid region, and there is no motivation to use the invention of cited reference 1 for detecting nucleic acid mutations.

CITATION LIST

Patent Literature

Patent Literature 1: JP-A 2016-049107

Non Patent Literature

Non Patent Literature 1:
Shendure, 2012, Nature Biotechnology 30, 1084-1094
Non Patent Literature 2:
Harayama, 2017, PLoS ONE 12(6): e0179165
Non Patent Literature 3:
Yu, 2014, PLoS ONE 9(6): e98282

Non Patent Literature 4:
Hua, 2017, J. Genet. Genomics, 44(4), 207-213
Non Patent Literature 5:
Mock, 2015, Nucleic Acids Res., 43(11): 5560-5571
Non Patent Literature 6:
Miyaoka, 2014, Nat. Methods 11(3): 291-293
Non Patent Literature 7:
Findlay, 2016, PLoS ONE 11(4): e0153901
Non Patent Literature 8:
Zhu, 2014, Scientific Reports 4, 6420
Non Patent Literature 9:
Dahlem, 2012, PLoS Genet., 8(8): e1002861
Non Patent Literature 10:
Young, 2015, Nucleic Acids Res., 43(9): e59
Non Patent Literature 11:
Ramlee, 2015, Sci, Rep. 5: 15587

SUMMARY OF INVENTION

Technical Problem

An object of the present invention is to provide a simple and inexpensive method for detecting a variation of a reference sequence in a target nucleic acid region. Another object of the present invention is to provide a method for detecting deletion, insertion, or substitution of one or more nucleotides.

Solution to Problem

[1] A method for detecting a variation of a reference sequence in a target nucleic acid region,
the method comprising the steps of:
performing a template-dependent nucleic acid amplification reaction for amplifying a region containing the reference sequence using, as a template, a nucleic acid containing the target nucleic acid region, in the presence of a 10 to 200 nucleotide single-stranded nucleic acid capable of hybridizing with the reference sequence in the target nucleic acid region, and
examining the presence or absence of an amplified product,
wherein the single-stranded nucleic acid is RNA or a chimeric nucleic acid composed of RNA and one or more different nucleic acids,
wherein the single-stranded nucleic acid contains a sequence complementary to the reference sequence, and
wherein the single-stranded nucleic acid has a higher complementarity to the reference sequence than to a variant sequence having a variation of the reference sequence.
[2] The detection method according to the above [1], wherein the variation of the reference sequence in the target nucleic acid region is deletion, insertion, or substitution of one or more nucleotides in the reference sequence.
[3] The detection method according to the above [1] or [2], wherein the template-dependent nucleic acid amplification reaction is any one selected from the group consisting of PCR, RT-PCR, LAMP, ICAN, NASBA, LCR, SDA, TRC method, TMA, and RPA.
[4] The detection method according to the above [3], wherein the template-dependent nucleic acid amplification reaction is PCR.
[5] The detection method according to the above [4], wherein the PCR contains a denaturation step, an annealing step, and an elongation step in a cycle.
[6] The detection method according to the above [5], wherein the annealing step and the elongation step are performed at the same temperature.
[7] The detection method according to any one of the above [1] to [6], wherein the single-stranded nucleic acid is 15 to 30 nucleotides in length.
[8] The detection method according to any one of the above [1] to [7], wherein the single-stranded nucleic acid is a single-stranded RNA.
[9] The detection method according to any one of the above [1] to [8], wherein the nucleic acid containing the target nucleic acid region is a nucleic acid obtained from a clinical sample of a subject.
[10] A method for screening for a cell having a variation of a reference sequence in a target nucleic acid region, the method comprising the steps of:
preparing a nucleic acid from a subject cell;
carrying out the detection method according to any one of the above [1] to [9] using the obtained nucleic acid as a template and determining the presence or absence of an amplified product; and
identifying the cell as having a variation of the reference sequence when the presence of the amplified product has been determined.
[11] A method for enriching a nucleic acid having a variation of a reference sequence in a target nucleic acid region, the method comprising the steps of:
preparing a nucleic acid from a subject cell population; and
carrying out the detection method according to any one of the above [1] to [9] using the obtained nucleic acid as a template and recovering an amplified product.
[12] A kit for use in the detection method according to any one of the above [1] to [9], the kit comprising a single-stranded nucleic acid, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region.
[13] A detection reagent for use in the detection method according to any one of the above [1] to [9], the detection reagent comprising a single-stranded nucleic acid, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region.

Advantageous Effects of Invention

The present invention provides a method for detecting a variation of a reference sequence in a target nucleic acid region, which method is characterized in that the variation of the reference sequence in the target nucleic acid region can be simply and highly accurately detected as a positive signal in an cost-effective or inexpensive manner and in that deletion, insertion, or substitution of one or more nucleotides can be detected.

BRIEF DESCRIPTION OF DRAWINGS

FIG. 10A shows the results of two-step PCR using, as templates, the genomic DNA extracted from cells having a 1-base deletion in one allele (C4) and the genomic DNA extracted from cells having a 2-base deletion in one allele (C6) in the presence of ORN_p16 in a two-step protocol at an annealing/elongation temperature of 62° C. or 70° C.

FIG. 10B shows the results of sequencing analysis of the amplified products obtained at the indicated annealing/elongation temperatures.

DESCRIPTION OF EMBODIMENTS

Figure 1:
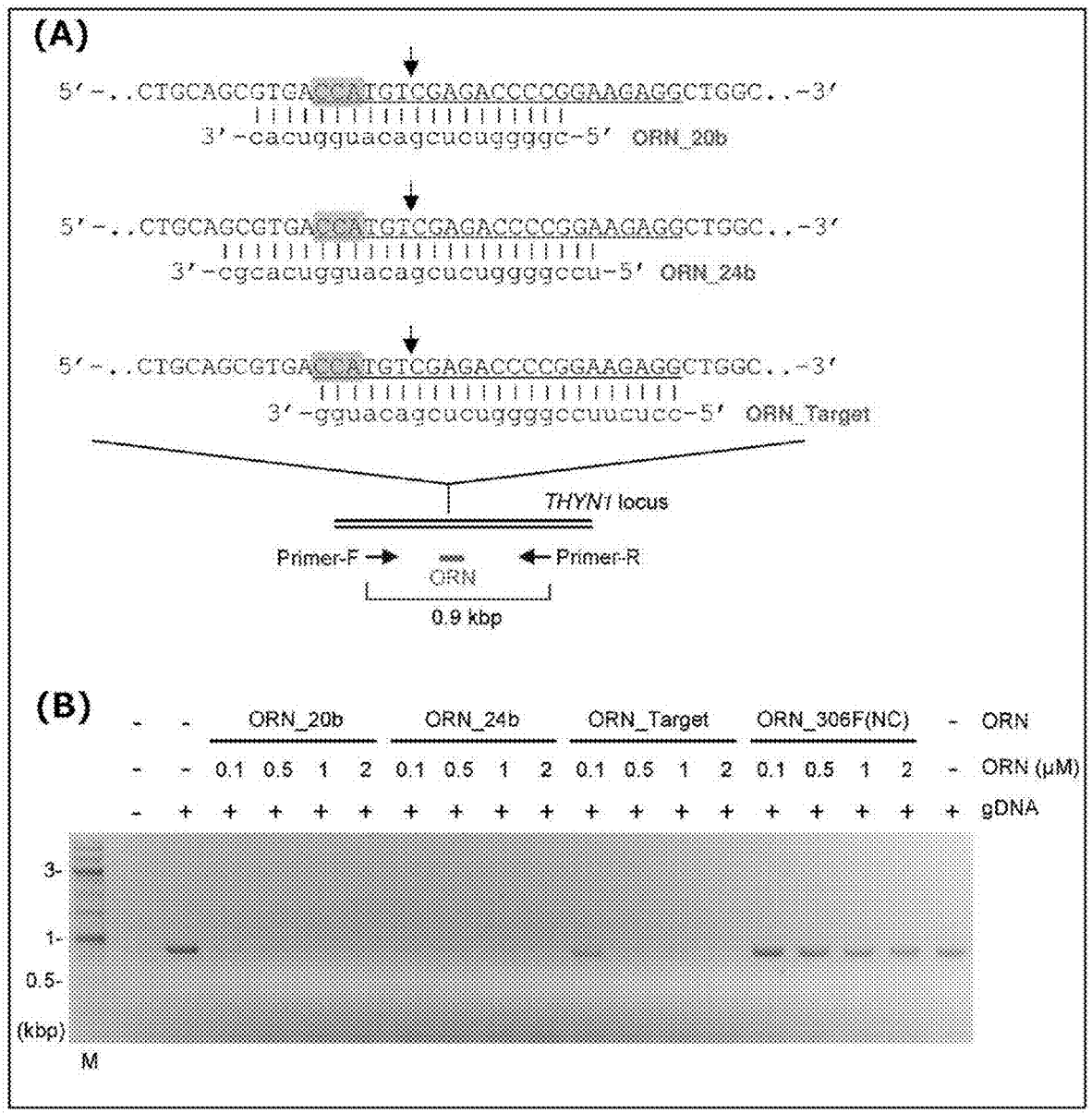
FIG. 1A shows the indicated oligoribonucleotides (ORN_20b, ORN_24b, and ORN_Target, see Table 1) each hybridized with the nucleotide sequence of the target nucleic acid region (SEQ ID NO: 35) containing a CRISPR cleavage site in the human THYN1 locus; and the region to be amplified using a THYN1-specific primer set.
FIG. 1B shows the results of PCR using, as a template, the genomic DNA extracted from wild-type cells in the presence of the indicated oligoribonucleotide.

The present invention provides a method for detecting a variation of a reference sequence in a target nucleic acid region (hereinafter referred to as the "detection method of the present invention"). The detection method of the present invention comprises the steps of:

performing a template-dependent nucleic acid amplification reaction for amplifying a region containing the reference sequence using, as a template, a nucleic acid containing the target nucleic acid region, in the presence of a 10 to 200 nucleotide single-stranded nucleic acid capable of hybridizing with the reference sequence in the target nucleic acid region, and examining the presence or absence of an amplified product.

In the detection method of the present invention, the event in the template-dependent nucleic acid amplification reaction differs depending on a test nucleic acid to be examined for the presence or absence of a variation of the reference sequence. That is, in the case where the test nucleic acid has no variation of the reference sequence in the target nucleic acid region, the single-stranded nucleic acid hybridizes with the template, thereby inhibiting amplification, and no amplified product is obtained; and in the case where the test nucleic acid has a variation of the reference sequence in the target nucleic acid region, amplification proceeds without being inhibited and an amplified product is obtained.

As used herein, the "reference sequence" is a sequence used as the reference for analysis for a variation and may be determined in accordance with the purpose. The length (nucleotide length) of the reference sequence is not particularly limited. Preferably, the reference sequence has an adequate length to ensure that it exists only in the target nucleic acid region but not in a non-target nucleic acid region, but the reference sequence may have a length to ensure that it exists infrequently in a non-target nucleic acid region. More specifically, the reference sequence is preferably 10 nucleotides or more, more preferably 15 nucleotides or more, and still more preferably 20 nucleotides or more in length.

The "target nucleic acid region" is a region containing a sequence to be analyzed for a variation of the reference sequence and may be determined in accordance with the location of the reference sequence. The variation of the reference sequence may be, for example, deletion mutation, insertion mutation, or substitution mutation in the reference sequence, or methylation of a base in the reference sequence. In the case where gene polymorphism is present in a nucleic acid, a variant of a specific sequence (reference sequence) in the nucleic acid is regarded as the sequence having a variation of the reference sequence. In the present specification, a sequence having a variation of the reference sequence is called "variant sequence".

The template-dependent nucleic acid amplification reaction as used herein is a process mediated by a nucleic acid polymerase for repeated complementary strand synthesis based on a template nucleic acid to amplify a nucleic acid chain of a desired region. The region to be amplified is a region containing the reference sequence, and the nucleotide length of the region to be amplified can be adjusted in accordance with the type of the template-dependent nucleic acid amplification reaction. The template nucleic acid may be a single strand or a double strand. The template nucleic acid may be DNA, RNA or a DNA-RNA hybrid. In addition, the template nucleic acid encompasses a nucleic acid in which a constituent nucleotide is substituted by an artificial nucleotide derivative, and a modified form of natural DNA or RNA as long as they serve as a template for complementary strand synthesis. Specific examples of the template nucleic acid include genomic DNA, cDNA, synthetic DNA, total RNA, mRNA, rRNA, miRNA, and synthetic RNA. In the detection method of the present invention, the template nucleic acid is intended to be a test nucleic acid to be examined for a variation of the reference sequence in the target nucleic acid region. The template nucleic acid can be obtained using known methods suitable for the type of the template nucleic acid.

In the case where the template nucleic acid is a nucleic acid harvested from a clinical sample of a subject (e.g., genomic DNA extracted from blood or biopsy tissue), the presence or absence of a mutation in a specific gene (e.g., oncogenes) and gene polymorphism in the subject can be detected by the detection method of the present invention. In addition, in the case where the template nucleic acid is a bisulfite-converted nucleic acid (bisulfite-converted DNA), methylated bases (methylated cytosines etc.) in the reference sequence can be detected by the detection method of the present invention. In the case of the detection of methylated bases in the reference sequence, the reference sequence may be a sequence complementary to a specific nucleotide sequence present in the target region in the bisulfite-converted nucleic acid (bisulfite-converted DNA).

The template-dependent nucleic acid amplification reaction preferably involves primer annealing to the template nucleic acid and subsequent nucleic acid elongation from the 3' end of the primer to amplify a nucleic acid chain. Examples of the template-dependent nucleic acid amplification reaction include, but are not limited to, Polymerase Chain Reaction (PCR: (White, T. J. et al., Trends Genet., 5, 185(1989)), Reverse Transcriptase-Polymerase Chain Reaction (RT-PCR: James W. Larrick, Trends in Biotechnology, 10, 146-152, 1992), Loop-mediated isothermal Amplification (LAMP: WO 2000/28082), Isothermal and Chimeric primer-initiated Amplification of Nucleic acids (ICAN: WO 2002/16639), Nucleic Acid Sequence-Based Amplification (NASBA: Japanese Patent No. 2650159), Ligase Chain Reaction (LCR: Barany, F., Proc. Natl. Acad. Sci. USA, Vol. 88, p. 189-193, 1991), Strand Displacement Amplification (SDA: JP-B 7-114718), Transcription-Reverse Transcription-Concerted method (TRC method: Nakaguchi Y. et al., J. Clin. Microbiol., vol. 42: p. 4248-4292 (2004)), Transcription-Mediated-Amplification (TMA: Sarrazin C. et al., J. Clin. Microbiol., vol. 39: p. 2850-2855 (2001)), and Recombinase Polymerase Amplification (RPA: Piepenburg, O., et al., PLoS Biol., 2006, vol. 4, e204). The detection method of the present invention employs any of these template-dependent nucleic acid amplification reactions, preferably PCR.

The primer used in the template-dependent nucleic acid amplification reaction can be determined in accordance with each particular nucleic acid amplification method. The primer suitable for each particular nucleic acid amplification method can be designed based on known techniques and can be produced by known methods. The reaction conditions of the template-dependent nucleic acid amplification reaction are not particularly limited as long as they allow the generation of a specific amplified product expected from the principle of each particular nucleic acid amplification method. The reaction conditions can be determined in the usual manner.

The single-stranded nucleic acid used in the detection method of the present invention is preferably RNA or a chimeric nucleic acid composed of RNA and one or more different nucleic acids and contains a sequence complementary to the reference sequence. More preferred is a single-stranded RNA. The nucleic acid as the component other than the RNA in the chimeric nucleic acid may be DNA, modified DNA, modified RNA, or the like. In the case where the single-stranded nucleic acid is a chimeric nucleic acid composed of RNA and one or more different nucleic acids, the nucleic acid as the component other than the RNA accounts for preferably 50% or less, more preferably 40% or less, still more preferably 30% or less, still more preferably 20% or less, still more preferably 10% or less, and still more preferably 5% or less of the total nucleotide length.

The single-stranded nucleic acid capable of hybridizing with the reference sequence in the target nucleic acid region can be designed based on the nucleotide sequence information of the target nucleic acid region containing the reference sequence. Such nucleotide sequence information is usually available from known databases (DDBJ/GenBank/EMBL etc.), but when the desired nucleotide sequence information is not acquired from known databases, the nucleotide sequence information of the target nucleic acid region containing the reference sequence may be obtained by a known sequencing method. In the case where the template nucleic acid is a double strand (e.g., double-stranded DNA consisting of a sense strand and an antisense strand), either strand may be used for hybridization with the above-mentioned single-stranded nucleic acid.

The length (nucleotide length) of the single-stranded nucleic acid is not particularly limited as long as it is equal to or longer than the length of the reference sequence. For example, the single-stranded nucleic acid is preferably 10 to 200 nucleotides, more preferably 10 to 150 nucleotides, more preferably 10 to 120 nucleotides, more preferably 10 to 100 nucleotides, more preferably 10 to 90 nucleotides, still more preferably 10 to 80 nucleotides, still more preferably 10 to 70 nucleotides, still more preferably 10 to 60 nucleotides, still more preferably 10 to 50 nucleotides, and still more preferably 15 to 30 nucleotides in length.

In the case where the single-stranded nucleic acid is equal in length (nucleotide length) to the reference sequence, the nucleotide sequence of the single-stranded nucleic acid may be completely identical to the complementary nucleotide sequence of the reference sequence; and alternatively may have one or more nucleotides that are different from the corresponding ones in the complementary nucleotide sequence of the reference sequence as long as the nucleotide sequence of the single-stranded nucleic acid is capable of hybridizing with the nucleotide sequence of the reference sequence. Preferably, the nucleotide sequence of the single-stranded nucleic acid is completely identical to the complementary sequence of the reference sequence. The single-stranded nucleic acid preferably has a higher complementarity to the reference sequence than to the variant sequence. As used herein, the "complementarity" refers to the identity between the complementary sequence of the reference sequence and the nucleotide sequence of the single-stranded nucleic acid. That is, when the complementary sequence of the reference sequence is completely identical to the nucleotide sequence of the single-stranded nucleic acid, the complementarity is 100%. Therefore, in the above preferable embodiment, it can be said that "the number of base-pair mismatches between the nucleotide sequence of the single-stranded nucleic acid and the reference sequence is preferably smaller than that between the nucleotide sequence of the single-stranded nucleic acid and the variant sequence".

In the case where the single-stranded nucleic acid is longer (more nucleotides in length) than the reference sequence, the same requirements as described above apply to a portion of the nucleotide sequence of the single-stranded nucleic acid which portion is capable of hybridizing with the reference sequence. The nucleotide sequence except for the portion capable of hybridizing with the reference sequence is not particularly limited and may be a sequence capable of hybridizing with a sequence adjacent to the reference sequence in the target nucleic acid region; or a sequence which does not hybridize with a sequence other than the reference sequence in the target nucleic acid region.

The single-stranded nucleic acid may be modified at the 5' end and/or 3' end. For example, the 5' end and/or the 3' end of the single-stranded nucleic acid may be deoxidized, phosphorylated, aminated, biotinylated, thiolated, cholesterolated, digoxigeninylated (DIGylated), quencher-labeled (labeled with BHQ-1, BHQ-3, etc.), fluorochrome-labeled (labeled with DNP, Cy3, Cy5, TAMRA, 6-FAM, etc.), or the like.

The nucleotide monomer (ribonucleotide, deoxyribonucleotide) of the single-stranded nucleic acid may be a nucleotide having a chemically modified sugar, base, and/or phosphate as long as the single-stranded nucleic acid is capable of hybridizing with the reference sequence in the target nucleic acid region. Examples of the nucleotide having a modified base include 5-position modified uridines or cytidines (e.g., 5-propynyluridine, 5-propynylcytidine, 5-methylcytidine, 5-methyluridine, 5-(2-amino)propyluridine, 5-halocytidine, 5-halouridine, 5-methyloxyuridine, etc.); 8-position modified adenosines or guanosines (e.g., 8-bromoguanosine etc.); deazanucleotides (e.g., 7-deazaadenosine etc.); and O- or N-alkyl nucleotides (e.g., N6-methyladenosine etc.). Examples of the nucleotide having a modified sugar include 2'-position modified nucleotide analogs in which the 2'-OH of the ribonucleotide is substituted by H, OR, R, a halogen atom, SH, SR, $NH_2$, NHR, $NR_2$ (in which R represents an alkyl, alkenyl or alkynyl group having 1 to 6 carbon atoms), CN or the like, and a 5'-phosphorylated nucleotide in which the 5'-terminus is mono-phosphorylated. Examples of the nucleotide having a modified phosphate include those in which a phosphoester bond to the adjacent ribonucleotide is substituted by a phosphorothioate bond.

The single-stranded nucleic acid can be artificially produced by a known chemical synthesis method. A single-stranded RNA can be produced by in vitro transcription from a template DNA.

The nucleic acid polymerase used in the template-dependent nucleic acid amplification reaction is not particularly limited, and an DNA polymerase and/or RNA polymerase suitable for each particular nucleic acid amplification method described above can be used. In the case where a DNA polymerase is used in the template-dependent nucleic acid amplification reaction, the DNA polymerase used is not particularly limited, and an DNA polymerase suitable for each particular nucleic acid amplification method described above can be used. For example, DNA polymerase I (Pol I), DNA polymerase α (Pol α), other DNA polymerases except for Pol I and Pol α, a mixed-type DNA polymerase (a mixture of several different types of DNA polymerases), or the like may be used. Particularly preferred is DNA polymerase α. DNA polymerase α is a DNA polymerase having 3'-5' exonuclease activity. Commercially available products of DNA polymerase θ include KOD DNA polymerase (Toyobo), Pyrobest DNA polymerase (Takara Bio), and Pfu DNA polymerase (Promega), and these are suitable for use in the present invention. When DNA polymerase α is used in the template-dependent nucleic acid amplification reaction, the template-dependent nucleic acid amplification reaction is preferably PCR.

The reaction mixture of the nucleic acid amplification reaction is not particularly limited as long as the composition of the reaction mixture allows the desired reaction to proceed. The reaction mixture usually contains a template nucleic acid, primers (primer set), a nucleic acid polymerase (DNA polymerase and/or RNA polymerase), and nucleotides used as substrates of the nucleic acid polymerase. In addition, the reaction mixture further contains a buffering reagent, a salt, etc., and if necessary, further contains an enzyme protecting reagent, a melting temperature (Tm) value regulator, a surfactant, etc. Examples of the buffering reagent include those having a buffering capacity in neutral-to-weakly alkaline conditions, such as Tris-HCl. The pH is adjusted around to an optimal pH for the selected nucleic acid polymerase. The salt is contained as appropriate for maintaining enzyme activity or for regulating Tm value of the nucleic acid, and specific examples include KCl, NaCl, $MgCl_2$, $MgSO_4$, and $(NH_4)_2SO_4$. Examples of the enzyme protecting reagent include bovine serum albumin and saccharides. Examples of the Tm value regulator include dimethyl sulfoxide (DMSO), formamide, and betaine (N,N,N-trimethylglycine). Examples of the surfactant include Tween 20 and Triton X. The detailed composition of the reaction mixture can be determined in the usual manner. For the determination of the detailed composition of the reaction mixture, it is preferable to perform preliminary examination using a particular combination of a template, primers, a nucleic acid polymerase, and a single-stranded nucleic acid.

The amount of the single-stranded nucleic acid contained in the template-dependent nucleic acid amplification reaction system is adjusted such that the single-stranded nucleic acid is present in the system at an appropriate concentration that would interfere with amplification from a template nucleotide sequence having no variation of the reference sequence but allow amplification from a template nucleotide sequence having a variation of the reference sequence. For the optimization of the amount of the single-stranded nucleic acid, it is preferable to perform preliminary examination in particular conditions in the selected nucleic acid amplification reaction. More specifically, for example, the concentration is preferably 2 µM or less, more preferably 1.5 µM or less, and still more preferably 1 µM or less. The minimum concentration is not particularly limited, but the concentration is preferably 10 nM or more, more preferably 50 nM or more, still more preferably 100 nM or more, and still more preferably 500 nM or more.

In the case where the template-dependent nucleic acid amplification reaction used in the detection method of the present invention is PCR, annealing at an appropriate temperature contributes to detecting 1-base deletion, 1-base insertion, or 1-base substitution. The annealing temperature is preferably determined in consideration of the Tm value of the portion of the nucleotide sequence of the single-stranded nucleic acid which portion is capable of hybridizing with the reference sequence. The Tm value can be calculated by known calculation methods, such as the nearest-neighbor method and the GC content method. Preferably, the Tm value is calculated by the following formula:

$$Tm=(a+u)\times 2+(g+c)\times 4$$

wherein a, u, g, and c indicate the numbers of corresponding bases A, U, G, and C, respectively.

The annealing temperature is, for example, preferably the Tm value calculated by the above formula, with a plus or minus of 10° C., more preferably with a plus or minus of 6° C., and still more preferably with a plus or minus of 3° C. More specifically, the annealing temperature preferably meets the following conditions: when there is no mismatch between the single-stranded nucleic acid and the reference sequence (partner for hybridization), nucleic acid amplification in the region containing the reference sequence is inhibited; and when there is a single mismatch, nucleic acid amplification in the region containing the reference sequence is less inhibited as compared with the case of no mismatch and an amplified product is obtained. For the determination of the annealing temperature, it is preferable to perform preliminary examination using a particular combination of a template, primers, a nucleic acid polymerase, and a single-stranded nucleic acid.

In the case where the template-dependent nucleic acid amplification reaction used in the detection method of the present invention is PCR, the standard three-step protocol (a cycle of denaturation, annealing, and elongation) may be employed, but the two-step protocol (a cycle of denaturation and annealing/elongation) is preferably used. In the case where the nucleotide sequence of the single-stranded nucleic acid hybridizes with the reference sequence at an annealing temperature but does not hybridize with the reference sequence at an elongation temperature, an amplified product may be obtained from a template having no mutation and false-positive results may occur. To eliminate the possibility of such false-positive results, the two-step protocol is employed and designed such that the single-stranded nucleic acid hybridizes with the reference sequence at an annealing/elongation temperature. For the optimization of the conditions in the two-step protocol, it is preferable to perform preliminary examination using a particular combination of a template, primers, a nucleic acid polymerase, and a single-stranded nucleic acid.

In the case where the template-dependent nucleic acid amplification reaction used in the detection method of the present invention is PCR, quantification PCR (real-time PCR, digital PCR, etc.) may be performed.

In the step of examining the presence or absence of an amplified product, the reaction mixture after the nucleic acid amplification reaction is examined for the amplified product by a known method. More specifically, for example, the reaction mixture after the nucleic acid amplification reaction is subjected to agarose gel electrophoresis, and the presence or absence of the band of the amplified product of the target region is checked. The presence of the amplified product of the target region indicates that the template nucleic acid used in the reaction has a mutation in the target nucleic acid region. In addition, sequencing analysis of the amplified product may be performed to confirm the presence of the mutation in the target nucleic acid region.

The detection method of the present invention, which is intended to detect a variation of the reference sequence in the target nucleic acid region, is suitable for detecting a mutation in cells subjected to genome-editing for introducing a mutation in a sequence-specific manner. In addition, the detection method of the present invention can be used to determine whether a specific gene (e.g., oncogenes) has a mutation. Furthermore, the detection method of the present invention can be used for polymorphism detection in animals and vegetables, for variety identification of animals and vegetables, etc.

In the detection method of the present invention, a positive signal appears when a sample has a variation of the reference sequence. This feature is useful for the detection of a heterozygous mutation and is a great advantage for the detection method of the present invention. More advantageously, the detection method of the present invention does not require an expensive instrument and can easily be carried out with an instrument commonly used in laboratories (PCR cycler etc.). In addition, the detection method of the present invention can be used for the detection of 1-base deletion, insertion, or substitution and is very useful. Furthermore, the detection method of the present invention, which is characterized in that a positive signal appears when a sample has a variation of the reference sequence, is available for the detection of a variation even in the case where only some of many cells have a variation of the reference sequence, and is greatly advantageous. Again, since a positive signal appears when a sample has a variation of the reference sequence, sequencing of the amplified product can reconfirm the presence or absence of the variation of the reference sequence.

The detection method of the present invention is useful in screening for a successfully mutated cell in a cell population subjected to treatment for introducing a mutation into the reference sequence in the target nucleic acid region. The detection method of the present invention is also useful in screening for a cell having polymorphism in a cell population having gene polymorphism. Therefore, the present invention provides a method for screening for a cell having a variation of a reference sequence in a target nucleic acid region. The screening method of the present invention comprises the following steps of:

(1) preparing a nucleic acid from a subject cell;
(2) carrying out the detection method of the present invention using the obtained nucleic acid as a template and determining the presence or absence of an amplified product; and
(3) identifying the cell as having a variation of the reference sequence when the presence of the amplified product has been determined.

In step (1), a nucleic acid is prepared from a subject cell. The method for preparing the nucleic acid from the subject cell is not particularly limited, and a known method can be used. The subject cell is not limited and may be any cell of interest to be examined for the presence or absence of a variation of the reference sequence in the target nucleic acid region. More specifically, preferable examples of the subject cell include a cell from a single clone isolated from a cell population subjected to treatment for introducing a mutation into the reference sequence in the target nucleic acid region; and a cell from a single clone isolated from a cell population having gene polymorphism. In the case where a cell population subjected to treatment for introducing a mutation into the reference sequence in the target nucleic acid region is used, such treatment is not limited and may be any treatment for introducing a mutation in a sequence-specific manner. For example, known genome-editing techniques are suitable in the present invention. The isolation of a single clone from the cell population can be performed by a known method.

Steps (2) and (3) can be performed according to the above description of the detection method of the present invention.

The detection method of the present invention is useful in enriching a nucleic acid having a variation of a reference sequence in a target nucleic acid region. Therefore, the present invention provides a method for enriching a nucleic acid having a variation of a reference sequence in a target nucleic acid region. The method of the present invention for enriching the nucleic acid comprises the following steps of:

(1) preparing a nucleic acid from a subject cell population; and
(2) carrying out the detection method of the present invention using the obtained nucleic acid as a template and recovering an amplified product.

In step (1), a nucleic acid is prepared from a subject cell population. The method for preparing the nucleic acid from the subject cell population is not particularly limited, and a known method can be used. The subject cell population is not limited and may be any cell population that is suspected to be a mixture of cells having a variation of the reference sequence in the target nucleic acid region and cells without such a variation. A preferable example is a cell population subjected to treatment for introducing a mutation into the reference sequence in the target nucleic acid region. In the case where a cell population subjected to treatment for introducing a mutation into the reference sequence in the target nucleic acid region is used, such treatment is not limited and may be any treatment for introducing a mutation in a sequence-specific manner. For example, known genome-editing techniques are suitable in the present invention. In step (1), a single clone is not isolated from the cell population, and the nucleic acid is prepared from the whole cell population.

Step (2) can be performed according to the description of the above detection method of the present invention. The method for recovering the amplified product is not particularly limited, and a known method can be used. For example, in the case where the presence or absence of the amplified product has been determined by agarose gel electrophoresis, a gel portion including the band of the amplified product may be cut out to recover the amplified product. The recovered amplified product may be subjected to any kind of analysis. For example, the recovered amplified product may be subjected to sequencing for mutational pattern analysis.

The present invention provides a kit for performing the detection method of the present invention. The kit of the present invention comprises a single-stranded nucleic acid, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region. Other components of the kit are not particularly limited, and for example, a tube(s) for the template-dependent nucleic acid amplification reaction, reagents (e.g., a DNA polymerase, a primer set for amplifying a region containing the reference sequence, a dNTP mixture, a buffer solution, etc.), an instruction manual etc. may be comprised in the kit. With the kit of the present invention, the detection method of the present invention can be simply and quickly performed.

The present invention provides a detection reagent for use in the detection method of the present invention. The detection reagent of the present invention comprises a single-stranded nucleic acid as an active ingredient, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region. Embodiments of the single-stranded nucleic acid are as described above in the detection method of the present invention.

EXAMPLES

Hereinafter, the present invention will be described in detail by examples, but the present invention is not limited thereto.

Oligoribonucleotides and Primers

The oligoribonucleotides (hereinafter referred to as "ORNs") and primers used in Examples were all chemically synthesized in Greiner. The ORNs and primers used are shown in Tables 1 and 2, respectively.

TABLE 11

| ORN | Sequence (5'-3') | Target locus | Number of nucleotides | SEQ ID No. |
|---|---|---|---|---|
| ORN_20b | cggggucucgacauggucac | human THYN1 | 20 | 1 |
| ORN_24b | uccggggucucgacauggu cacgc | human THYN1 | 24 | 2 |
| ORN_Target | ccucuuccggggucucgacaugg | human THYN1 | 23 | 3 |
| ORN_302F(NC) | ccggggcgcugggcugucccc | human IRF-1 | 21 | 4 |
| ORN_306F(NC) | ggggccggggcgcugggcugu ccc | human IRF-1 | 25 | 5 |
| ORN_Gx5 | caccuccucuacccgaccccc | human CDKN2A (p16) | 21 | 6 |
| ORN_p16 | gcggcccggggucggguaga | human CDKN2A (p16) | 20 | 7 |
| crRNA_hTHYN1 | ccucuuccggggucucgacag uuuuagagcuaugcuguuuug | human THYN1 | 42 | 8 |
| crRNA_NC | cggcaggcucgggugcgccug uuuuagagcuaugcuguuuug | chicken Pax5 | 42 | 9 |
| ORN_Tax | auauacggaguuaaggugua | mouse Tax1bp1 | 20 | 10 |
| ORN_FOS | gcgccgcagccacugcuuuu | human c-FOS | 20 | 11 |
| ORN_EGFR_L858 | caguuuggccagcccaaaauc | human EGFR | 21 | 12 |

TABLE 2

| Primer | Sequence (5'-3') | SEQ ID No. |
|---|---|---|
| hTHTN1-gRNA-target-15-F3 | agccagcaaattacttcatcatc | 13 |
| hTHTN1-gRNA-target-15-R3 | ctcctcctccatccacttagaat | 14 |
| hTHTN1-gRNA-target-15-F4 | ctgcagcgtgaccatgtc | 15 |
| hTHTN1-gRNA-target-15-F2 | cacccaacaaaagtgtctctgtg | 16 |

TABLE 2-continued

| Primer | Sequence (5'-3') | SEQ ID No. |
|---|---|---|
| hTHYN1-gRNA-target-15-R2 | gttctcaaaaagcagggagtgaa | 17 |
| hTHYN1-gRNA-target-15-F5 | ccgcagtcgagtctgcagagtgttgg | 18 |
| hTHYN1-gRNA-target-15-R5 | caaggctgggctcaaattccacatcc | 19 |
| hTHYN1-gRNA-target-15-F6 | cggggtctcgacatggtcac | 20 |
| hCDKN2A-(-)Bisul-F2 | gaggggctggctggtcaccaga | 21 |
| hCDKN2A-(-)Bisul-R2 | tgcagaccctctacccacctggat | 22 |
| hCDKN2A-ORN-F | ccccgattcaatttggcagttagga | 23 |
| hCDKN2A-ORN-R | attacaaacccttctgaaaaactcc | 24 |
| human_PD-L1_prom-F | actccatgctcctgccaaat | 25 |
| human_PD-L1_prom-R | ccagcgagctagccagagat | 26 |
| hCycD1-prom-seq-F | ccgaagagtctccaggctagaag | 27 |
| hCycD1-prom-seq-R | acctccttctgcacacatttgaa | 28 |
| mTax1bp1-exon2-F2 | ttgactgagttgtatccccatcc | 29 |
| mTax1bp1-exon2-R2 | tgcacagtgtttagtatttcatggtg | 30 |
| hc-fos-prom-F | aactgtcttcagtttccgtacaagg | 31 |
| hc-fos-prom-R | gggtgagtggtagtaagagaggcta | 32 |
| hEGFR-Exon21-F | gccttccatctttggatcag | 33 |
| hEGFR-Exon21-R | ctgcagggagaagactgaaacct | 34 |

Cells and Genomic DNA Extraction

Raji cells were cultured in RPMI-1640 (Wako) supplemented with 10% fetal bovine serum (FBS). 293T cells were cultured in DMEM (Wako) supplemented with 10% FBS. HCT116 cells were cultured in McCoy's 5A (Thermo Fisher Scientific) supplemented with 10% FBS. Ba/F3 cells were cultured in RPMI-1640 supplemented with 10% FBS, 10 mM HEPES buffer (pH 7.2), 1× non-essential amino acids, 1 mM sodium pyruvate, 5 µM 2-mercaptoethanol, and 1 ng/mL IL-3. NCI-H1975 cells were cultured in RPMI-1640 supplemented with 10% FBS. Genomic DNAs were extracted from the cells by a standard phenol/chloroform extraction technique.

PCR Conditions

For PCR targeting the human THYN1 locus, a PCR reaction mixture containing 20 ng of the Raji cell genomic DNA, 0.3 µM each primer, and 0.1 to 2 µM ORN was prepared in a 10 µL volume according to the manufacturer's protocol. The reaction was carried out with an initial denaturation at 94° C. for 2 min, followed by 35 cycles of 98° C. for 10 sec, 62° C. for 30 sec, and 68° C. for 1 min.

For PCR targeting the human CDKN2A(p16) locus, a PCR reaction mixture containing 20 ng of the 293T or HCT116 cell genomic DNA, 0.3 µM each primer, and 1 µM ORN was prepared in a 10 µL volume. The reaction in Example 2 was carried out with an initial denaturation at 94° C. for 2 min, followed by 30 cycles of 98° C. for 10 sec, 62° C. for 30 sec, and 68° C. for 1 min. The reaction in Example 3 was carried out with an initial denaturation at 94° C. for 2 min, followed by 30 cycles of the following 2 steps: 98° C. for 10 sec, and 62 to 72° C. for 20 sec.

For PCR targeting both the human THYN1 and CDKN2A (p16) loci, a PCR reaction mixture containing 20 ng of the 293T cell genomic DNA, 0.3 µM each primer, and 1 µM each ORN was prepared in a 10 µL volume. The reaction was carried out with an initial denaturation at 94° C. for 2 min, followed by 30 cycles of 98° C. for 10 sec, 62° C. for 30 sec, and 68° C. for 1 min. The reaction in Example 3 was carried out with an initial denaturation at 94° C. for 2 min, followed by 30 cycles of 98° C. for 10 sec, 62° C. for 30 sec, and 68° C. for 1 min or with an initial denaturation at 94° C. for 2 min, followed by 30 cycles of the following 2 steps: 98° C. for 10 sec, and 68° C. for 1 min 30 sec.

For PCR targeting the mouse Tax1bp1 locus, a PCR reaction mixture containing 20 ng of the Ba/F3 cell genomic DNA, 0.3 µM each primer, and 1 µM ORN was prepared in a 10 µL volume. The reaction in Example 4 was carried out with an initial denaturation at 94° C. for 2 min, followed by 30 cycles of the following 2 steps: 98° C. for 10 sec, and 50 to 65° C. for 80 sec.

For PCR targeting the human c-FOS locus, a PCR reaction mixture containing 20 ng of the 293T cell genomic DNA, 0.3 µM each primer, and 1 µM ORN was prepared in a 10 µL volume. The reaction in Example 4 was carried out with an initial denaturation at 94° C. for 2 min, followed by 30 cycles of the following 2 steps: 98° C. for 10 sec, and 50 to 68° C. for 80 sec. The reaction in Example 5 was carried out with an initial denaturation at 94° C. for 2 min, followed by 30 cycles of the following 2 steps: 98° C. for 10 sec, and 65° C. for 80 sec.

For PCR targeting the human EGFR locus, a PCR reaction mixture containing 20 ng of the 293T or NCI-H1975 cell genomic DNA, 0.3 µM each primer, and 1 µM ORN was prepared in a 10 µL volume. The reaction in Example 6 was carried out with an initial denaturation at 94° C. for 2 min, followed by 30 cycles of the following 2 steps: 98° C. for 10 sec, and 59 to 65° C. for 70 sec.

The PCR products were electrophoresed on a 1% or 2% agarose gel, and if necessary, subjected to DNA sequencing. DNA sequencing data were analyzed using Applied Biosystems Sequence Scanner Software v2.0 (Thermo Fisher Scientific).

Real-Time PCR Conditions

KOD SYBR qPCR Mix (Toyobo) was used for real-time PCR. A PCR reaction mixture containing 20 ng of the genomic DNA, 0.2 µM each primer, and 0.25 µM ORN was prepared in a 10 µL volume according to the manufacturer's protocol. The reaction was carried out with an initial denaturation at 98° C. for 2 min, followed by 30 cycles of 98° C. for 10 sec, 62° C. for 30 sec, and 68° C. for 1 min. The reaction and quantification were performed using 7900HT Fast Real-Time PCR System (Applied Biosystems). The PCR products were electrophoresed on a 1% agarose gel to confirm that the amplified products of expected sizes were obtained.

Plasmids

The Cas9 expression plasmid (Addgene #41815) and chimeric single guide RNA (sgRNA) expression plasmid (Addgene #41824) were provided by Dr. George Church through Addgene. To construct an sgRNA expression plasmid targeting the human THYN1 locus, a CRISPR target sequence was cloned downstream of the U6 promoter in the sgRNA expression plasmid according to the hCRISPR gRNA synthesis protocol (media.addgene.org/data/93/40/adf4a4fe-5e77-11e2-9c30-003048dd6500.pdf). To construct a Cas9 plus sgRNA expression plasmid targeting the human CDKN2A(p16) locus, the sgRNA expression cassette for CDKN2A(p16) (Gx4 #2) was cloned upstream of the Cas9 expression cassette in the Cas9 expression plasmid.

CRISPR-Mediated Genome Editing

For genome editing of the human THYN1 locus, Raji cells (1×10⁷) were transfected with the Cas9 expression plasmid (120 µg), the sgRNA expression plasmid targeting the human THYN1 locus (120 µg), and pEGFP-N3 (0.3 µg, Clontech) by electroporation on a Gene Pulser II (Bio-Rad) at 250 V and 950 FF. One day later, GFP-positive cells were individually sorted and expanded.

For genome editing of the human CDKN2A(p16) locus, 293T cells (4×10⁵) were transfected with the Cas9 plus sgRNA expression plasmid targeting the human CDKN2A (p16) locus (4 µg) and pcDNA3.1/Hygro(−) (0.4 µg, Thermo Fisher Scientific) using Lipofectamine 3000 (Thermo Fisher Scientific). Two days later, hygromycin was added (0.4 mg/ml), and hygromycin-resistant colonies were picked and cultured.

For genome editing of the human THYN1 and CDKN2A (p16) loci, 293T cells (4×10⁵) were transfected with the Cas9 plus sgRNA expression plasmid targeting the human CDKN2A(p16) locus (4 µg), the sgRNA expression plasmid targeting the human THYN1 locus (4 µg), and pcDNA3.1/Hygro(−) (0.4 µg) using Lipofectamine 3000. Two days later, hygromycin was added (0.4 mg/ml), and hygromycin-resistant colonies were picked and cultured.

TALEN-Mediated Genome Editing

For genome editing of the human c-FOS locus, 293T cells (4×10⁵) were transfected with TALEN plasmids targeting the human c-FOS locus (TALEN-left, TALEN-right, 4 µg each) and pcDNA3.1/Hygro(−) (0.4 µg, Thermo Fisher Scientific) using Lipofectamine 3000 (Thermo Fisher Scientific). Two days later, hygromycin was added (0.4 mg/ml), and hygromycin-resistant colonies were picked and cultured.

Example 1: Detection of Mutation in Human THYN1 Locus (1-1) Inhibition of PCR Amplification by Human THYN1 Locus-Targeting ORNs The ORNs used were ORN_20b, ORN_24b, and ORN_Target (see Table 1).

FIG. 1A shows the indicated oligoribonucleotides each hybridized with the nucleotide sequence of the target nucleic acid region (CTGCAGCGTGACCATGTCGAGACCCCG-GAAGAGGCTGGC (SEQ ID NO: 35)) containing a CRISPR cleavage site in the human THYN1 locus; and the region to be amplified using a THYN1-specific primer set. In the figure, the CRISPR target site (reference sequence) is underlined, a protospacer adjacent motif (PAM) is shaded, and the CRISPR cleavage site is shown by an arrow. ORN_20b and ORN_24b hybridize with their respective target sites with the center of each ORN sequence being aligned with the CRISPR cleavage site, which is 3-bp upstream of the PAM. ORN_Target matches the sgRNA sequence and the PAM sequence used for genome editing.

These ORNs, the genomic DNA of Raji cells, a THYN1-specific primer set (hTHYN1-gRNA-target-15-F3 and hTHYN1-gRNA-target-15-R3, see Table 2), and KOD DNA polymerase (KOD-Plus-Ver. 2 (Toyobo)) were used to amplify a 0.9-kbp region surrounding the target sequence under the PCR conditions described above. The results are shown in FIG. 1B. When the genomic DNA extracted from human Raji cells was used for PCR in the absence of any of the ORNs, the 0.9-kbp region was specifically amplified. The addition of 0.1 to 2 µM ORN 20b or ORN_24b to the reaction mixture strongly inhibited amplification. The addition of 0.5 to 2 µM ORN_Target to the reaction mixture also inhibited amplification. In contrast, ORN_306F(NC), an ORN hybridizable with an irrelevant locus (human IRF-1 locus), did not affect amplification. These results show that the addition of ORNs hybridizable with the reference sequence in a target nucleic acid region to a PCR reaction mixture specifically inhibited PCR amplification of the target nucleic acid region.

(1-2) Detection of Genome-Edited Cells

We investigated how an ORN hybridizable with the reference sequence in a target nucleic acid region affects PCR amplification from a template having a mutation in the target nucleic acid region.

We performed CRISPR-mediated genome editing of the THYN1 locus in Raji cells and established five types of genome-edited clones (T1, T4, T6, T7 and T9) in which the reference sequence was mutated in both alleles. These five genome-edited clones have different mutations in the nucleotide sequence of a target nucleic acid region containing a CRISPR cleavage site in the wild-type human THYN1 locus. The nucleotide sequence of the target nucleic acid region is GCACTAAAGTCCCCTGCAGCGTGAC-CATGTCGAGACCCCGGAAGAGGCTGGC (SEQ ID NO: 36; the CRISPR target site (reference sequence) is underlined, PAM is CCA at positions 25 to 27, and the CRISPR cleavage site is between T at position 30 and C at position 31). The mutations are as follows.

T1: The nucleotides at positions 9 to 30 of the nucleotide sequence of SEQ ID NO: 36 are deleted in one allele, and 115 nucleotides are inserted in the CRISPR cleavage site in the other allele.

T4: The nucleotides at positions 24 to 30 of the nucleotide sequence of SEQ ID NO: 36 are deleted in both alleles.

T6: The nucleotides at positions 21 to 36 of the nucleotide sequence of SEQ ID NO: 36 are deleted in one allele, and the nucleotides at positions 30 to 32 are deleted in the other allele.

T7: The nucleotides at positions 27 to 37 of the nucleotide sequence of SEQ ID NO: 36 are deleted in one allele, and the nucleotides at positions 31 to 36 are deleted in the other allele.

T9: The same sequence of 501 nucleotides are inserted in the CRISPR cleavage site in both alleles.

Figure 2:
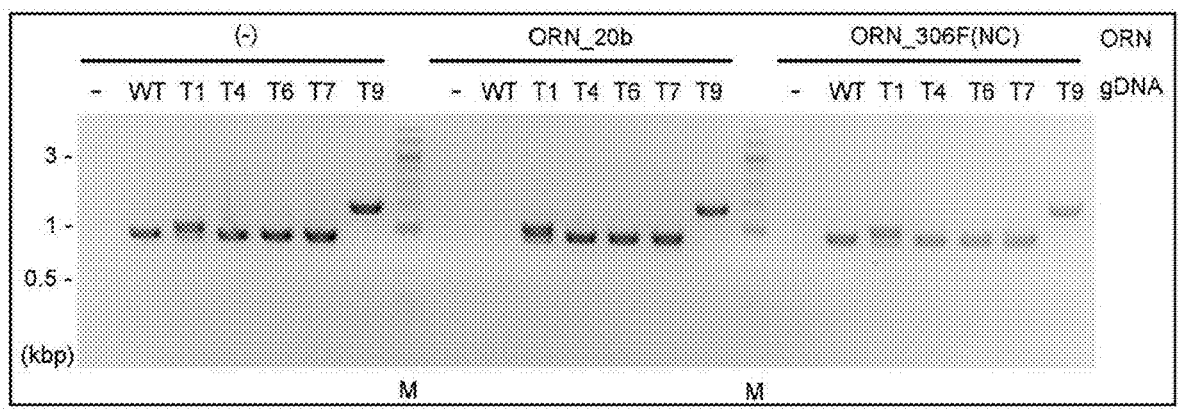
FIG. 2 shows the results of PCR using, as templates, the genomic DNAs extracted from wild-type cells (WT) and 5 types of genome-edited cells (T1, T4, T6, T7, and T9) in the presence of the indicated oligoribonucleotide (ORN_20b or ORN_306F(NC), see Table 1).

PCR was performed on the genomic DNAs extracted from wild-type cells and the genome-edited clones, using a THYN1-specific primer set (hTHYN1-gRNA-target-15-F3 and hTHYN1-gRNA-target-15-R3, see Table 2) and KOD DNA polymerase (KOD-Plus-Ver. 2) in the presence or absence of ORNs. The ORNs used were ORN_20b and ORN_306F(NC) (see Table 1). The results are shown in FIG. 2. The left panel shows the results for the absence of ORNs, the center panel shows the results for the presence of ORN_20b, and the right panel shows the results for the presence of ORN_306F(NC). In the absence of ORNs, the target nucleic acid region was amplified from the genomic DNAs of the wild-type cells (WT) and all the genome-edited cells. In the presence of ORN_20b, amplification from the genomic DNA of the wild-type cells (WT) was completely inhibited, whereas amplification from the genome-edited cells was not inhibited. ORN_306F(NC), an ORN hybridizable with an irrelevant locus (human IRF-1 locus), did not affect amplification.

There was a possibility that ORN_20b might allele-specifically inhibit PCR amplification from the genomic DNA of cells in which the CRISPR target site in each allele is differently mutated. This possibility was examined by sequencing analysis of the PCR products obtained by amplification from the genomic DNAs of T1, T6, and T7 cells, in which the CRISPR target site in each allele is differently mutated, in the presence or absence of ORN_20b. As a result, two sequencing signals were detected in each PCR product obtained in the presence of ORN_20b, and the same signals were detected in the corresponding PCR product obtained in the absence of ORN_20b. These results demonstrate that ORN_20b did not affect amplification from those genomic DNAs.

Figure 3:
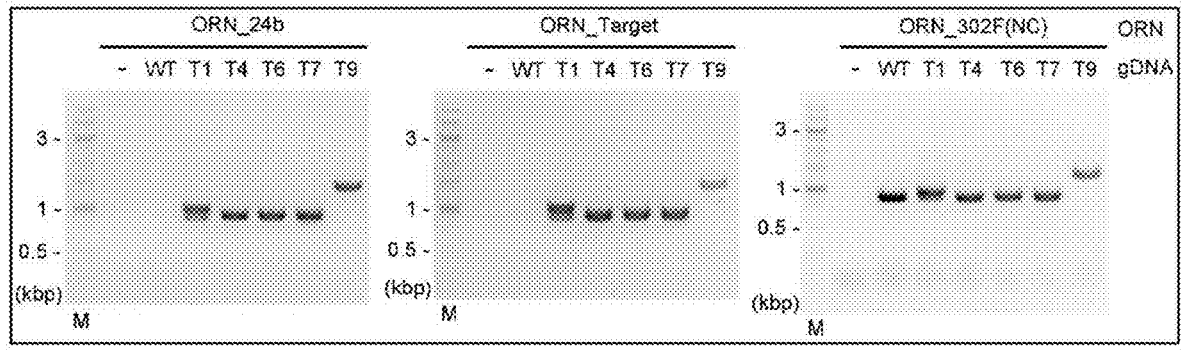
FIG. 3 shows the results of PCR using, as templates, the genomic DNA extracted from wild-type cells (WT) and 5 types of genome-edited cells (T1, T4, T6, T7, and T9) in the presence of the indicated oligoribonucleotide (ORN_24b, ORN_Target, or ORN_302F(NC), see Table 1).

Next, PCR was performed using other ORNs (ORN_24b, ORN_Target and ORN_302F(NC), see Table 1) under the same conditions as above. The results are shown in FIG. 3. The left panel shows the results for the presence of ORN_24b, the center panel shows the results for the presence of ORN_Target, and the right panel shows the results for the presence of ORN_302F(NC). The band pattern obtained by PCR in the presence of ORN_24b or ORN_Target was the same as that obtained by PCR in the presence of ORN_20b. ORN_302F(NC), a 21-base ORN hybridizable with an irrelevant locus (human IRF-1 locus), did not affect amplification.

These results show that PCR performed in a reaction mixture containing an ORN capable of hybridizing with the reference sequence in a target nucleic acid region is effective for distinguishing a wild-type nucleic acid sequence having no mutation in the target nucleic acid region (reference sequence) from a mutated nucleic acid sequence having bi-allelic indel mutations in the target nucleic acid region (variant sequence).

(1-3) Detection of Mono-Allelic Mutations

In the above (1-2), PCR was performed on the genomic DNA extracted from genome-edited cells having bi-allelic indel mutations. In this study, we investigated whether PCR could distinguish a mutated nucleic acid sequence having a mutation only in one allele (mono-allelic mutation) from a wild-type nucleic acid sequence (reference sequence). To this end, the genomic DNA extracted from wild-type cells and the genomic DNA extracted from T4 or T9 cells, which had a mutation common to both alleles, were mixed at a ratio of 1:1 to simulate a mono-allelic mutation. PCR was performed on the genomic DNA extracted from wild-type cells (WT), the genomic DNA extracted from T4 or T9 cells, a mixture of WT and T4 genomic DNAs, and a mixture of WT and T9 genomic DNAs, using a THYN1-specific primer set (hTHYN1-gRNA-target-15-F3 and hTHYN1-gRNA-target-15-R3, see Table 2) and KOD DNA polymerase (KOD-Plus-Ver. 2) in the presence or absence of ORNs. The ORNs used were ORN_20b, ORN_24b, ORN_Target, ORN_302F(NC), and ORN_306F(NC) (see Table 1).

Figure 4:
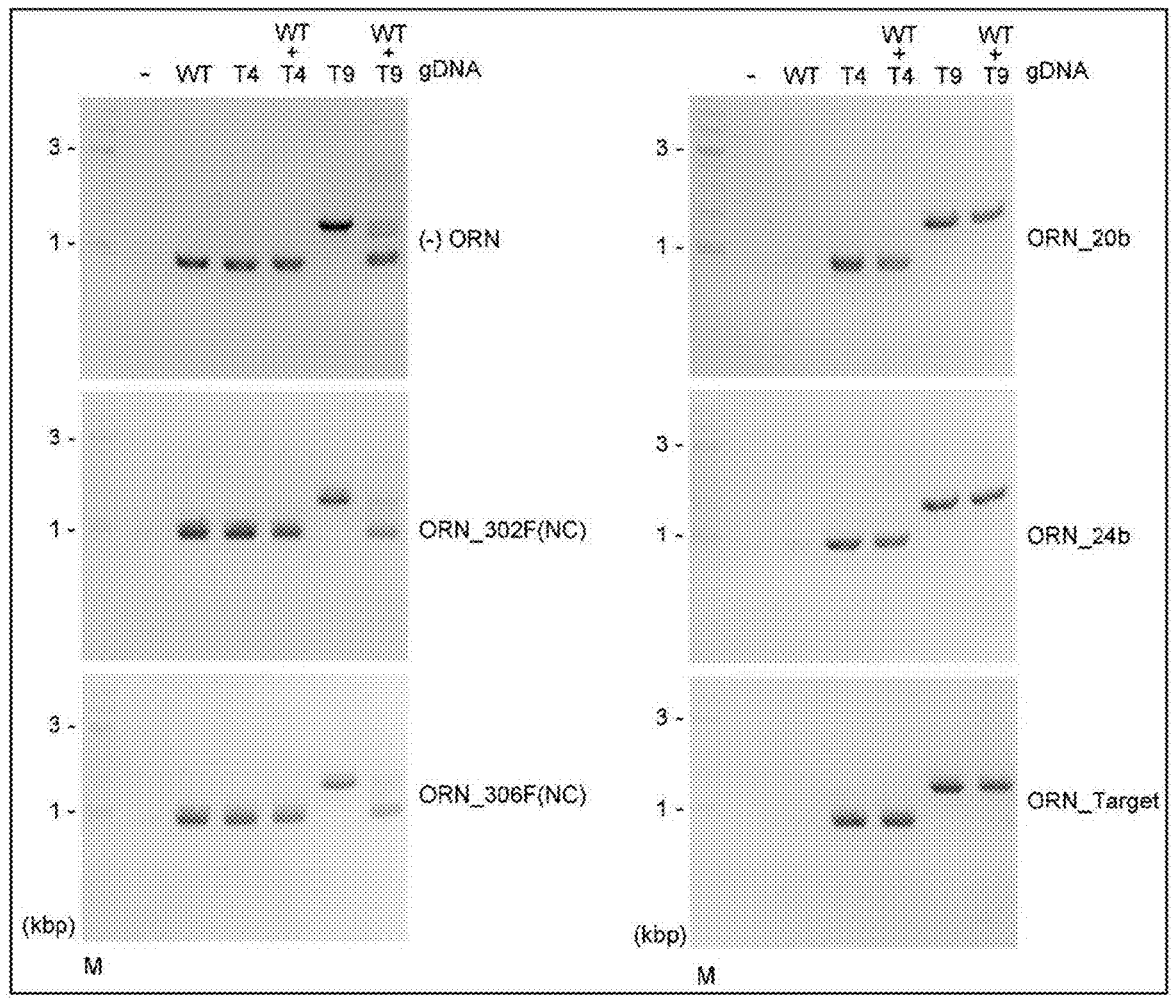
FIG. 4 shows the results of PCR using, as templates, the genomic DNA extracted from wild-type cells (WT), the genomic DNA extracted from cells having a mutation common to both alleles (T4 or T9), and a 1:1 mixture of WT and T4 or T9 genomic DNAs (WT+T4, WT+T9), which simulates a mono-allelic mutation, in the presence of the indicated oligoribonucleotide (ORN_20b, ORN_24b, ORN_Target, ORN_302F(NC), or ORN_306F(NC), see Table 1).

The results are shown in FIG. 4. ORN_20b, ORN_24b, and ORN_Target each inhibited PCR amplification from a template containing the wild-type (WT) genomic DNA alone, not containing the mutated genomic DNA. When the mixture of WT and T4 genomic DNAs or the mixture of WT and T9 genomic DNAs was used, a single band was detected, which band had the same size as that observed in the amplification from the T4 genomic DNA alone or the T9 genomic DNA alone. In addition, the PCR product (0.9 kb) obtained by amplification from the mixture of WT and T4 genomic DNAs in the presence of ORN_20b was sequenced. As a result, the PCR product showed the same sequencing signal as that of the amplified product from the T4 genomic DNA, not the WT genomic DNA. These results show that PCR performed in a reaction mixture containing an ORN capable of hybridizing with the reference sequence in a target nucleic acid region is effective for distinguishing a wild-type nucleic acid sequence having no mutation in the target nucleic acid region (reference sequence) from a mutated nucleic acid sequence having a mono-allelic indel mutation in the target nucleic acid region (variant sequence).

(1-4) Detection of Genome-Edited Cells by PCR Using Pfu DNA Polymerase

Pfu DNA polymerase is a DNA polymerase α having 3'-5' exonuclease activity, which is a function in common with KOD DNA polymerase (KOD-Plus-Ver. 2) used in Example 1. In this study, PCR was performed under the same conditions as in the above (1-2) and (1-3) except for using Pfu DNA polymerase instead of KOD DNA polymerase (KOD-Plus-Ver. 2). More specifically, PCR was performed on the genomic DNA extracted from wild-type cells (WT), the genomic DNA extracted from T1, T4, T6, T7 or T9 cells, a mixture of WT and T4 genomic DNAs, and a mixture of WT and T9 genomic DNAs, using a THYN1-specific primer set (hTHYN1-gRNA-target-15-F3 and hTHYN1-gRNA-target-15-R3, see Table 2) and Pfu DNA polymerase in the presence or absence of ORNs. The ORNs used were ORN_20b, ORN_24b, and ORN_306F(NC) (see Table 1).

Figure 5:
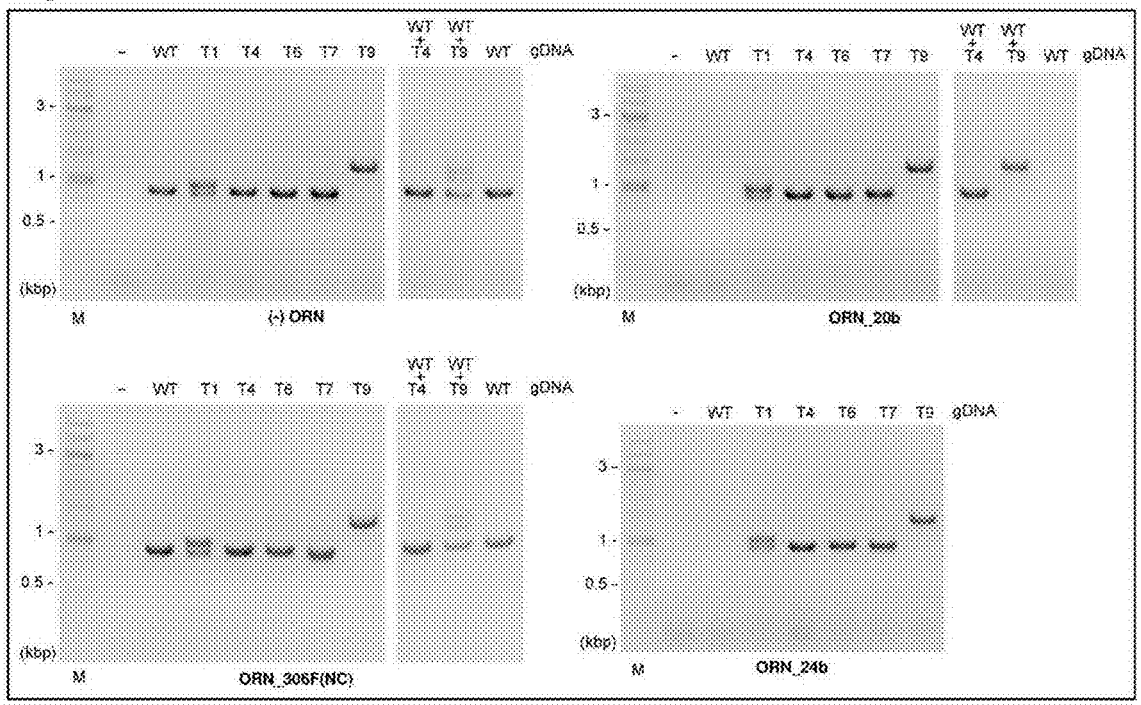
FIG. 5 shows the results of PCR performed under the same conditions as in Example 1 (1-2) and (1-3) except for using Pfu DNA polymerase instead of KOD DNA polymerase.

The results are shown in FIG. 5. As with the case using KOD DNA polymerase, ORN_20b and ORN_24b each inhibited amplification of the target nucleic acid region from the WT genomic DNA, but allowed amplification of the target nucleic acid region from the genomic DNAs having a mutation in the reference sequence.

(1-5) Detection of Genome-Edited Cells by Real-Time (Quantification) PCR

In this study, we investigated whether real-time PCR could distinguish a mono-allelic indel mutation from bi-allelic indel mutations.

Real-time PCR was performed on the genomic DNA extracted from wild-type cells (WT), the genomic DNA extracted from T4 or T6 cells, which had bi-allelic mutations, and a mixture of WT and T4 genomic DNAs, which simulated a mono-allelic mutation, using a THYN1-specific primer set (hTHYN1-gRNA-target-15-F3 and hTHYN1-gRNA-target-15-R3, see Table 2) and KOD DNA polymerase (KOD SYBR qPCR Mix) in the presence of ORN_24b or ORN_302F(NC) or in the absence of ORNs.

Figure 6:
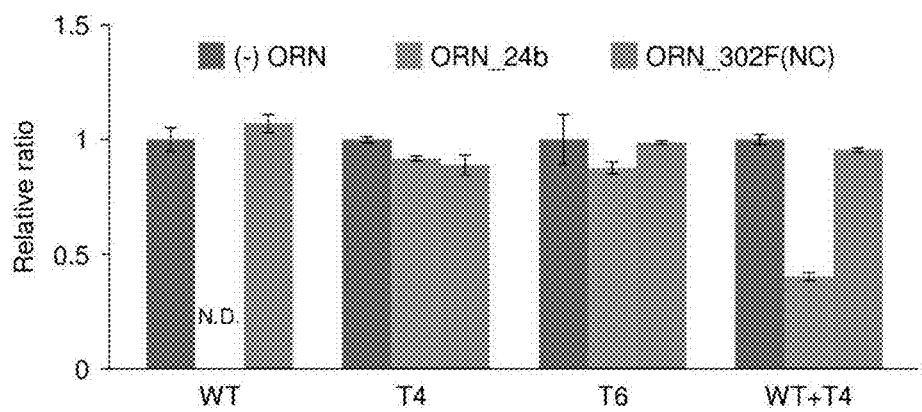
FIG. 6 shows the results of real-time PCR using, as templates, the genomic DNA extracted from wild-type cells (WT), the genomic DNA extracted from cells having bi-allelic mutations (T4 or T6), and a genomic DNA simulating a mono-allelic mutation (WT+T4), in the presence of the indicated oligoribonucleotide (ORN_24b or ORN_302F (NC)).

The results are shown in FIG. 6. The results of the real-time PCR in the presence of ORN_24b show that amplification of the target nucleic acid region from the WT genomic DNA was not detected, whereas amplification of the target nucleic acid region from the genomic DNA of T4 or T6 cells was not affected. In addition, amplification of the target nucleic acid region from the template simulating a mono-allelic indel mutation (WT+T4) was inhibited by about 60%. ORN_302F(NC), an ORN hybridizable with an irrelevant locus (human IRF-1 locus), did not affect amplification. These results show that real-time PCR performed in a reaction mixture containing an ORN capable of hybridizing with the reference sequence in a target nucleic acid region is effective for distinguishing between a wild-type nucleic acid sequence having no mutation in the target nucleic acid region (reference sequence), a mutated nucleic acid sequence having bi-allelic indel mutations in the target nucleic acid region (variant sequence), and a mutated nucleic acid sequence having a mono-allelic indel mutation in the target nucleic acid region (variant sequence).

(1-6) Examination of PCR Using CRISPR RNA

Genome editing can be performed by transfection of recombinant CRISPR ribonucleoproteins (RNPs). In this approach, synthesized sgRNAs or complexes of CRISPR RNAs (crRNAs) plus trans-activating crRNAs (tracrRNAs) are used as gRNAs. In the genome editing using CRISPR RNPs, the use of crRNAs rather than target-specific ORNs would be more cost-effective for detecting genome-edited cells. In this study, PCR was performed using crRNAs instead of target-specific ORNs. The crRNAs used were a crRNA containing an RNA sequence complementary to the CRISPR target site (crRNA_Target: SEQ ID NO: 8, see Table 1) and a control crRNA containing an RNA sequence complementary to an irrelevant locus (chicken Pax5 locus) (crRNA N.C.: SEQ ID NO: 9, see Table 1). PCR was performed on the genomic DNA extracted from wild-type cells (WT), the genomic DNA extracted from T4 or T6 cells, and a mixture of WT and T4 genomic DNAs, using a THYN1-specific primer set (hTHYN1-gRNA-target-15-F3 and hTHYN1-gRNA-target-15-R3, see Table 2) and KOD DNA polymerase (KOD-Plus-Ver. 2) in the presence of either of the two crRNAs.

Figure 7:
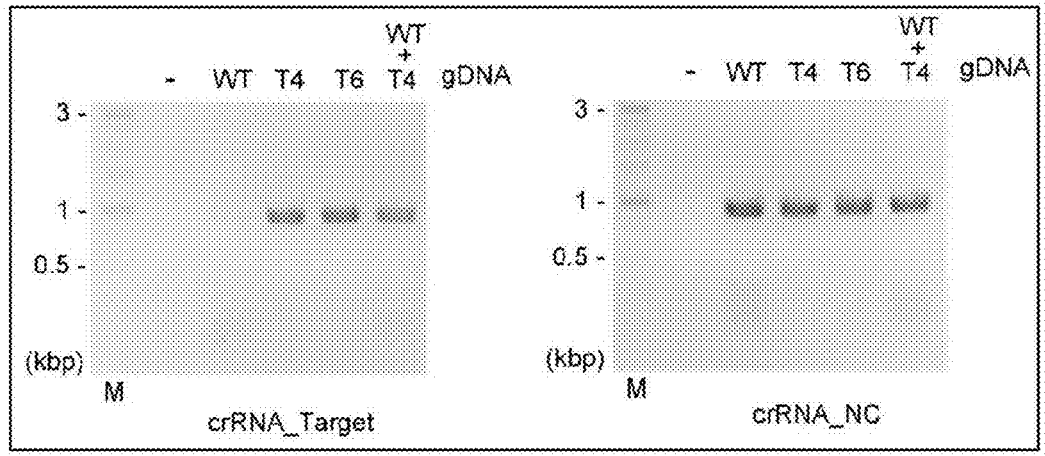
FIG. 7 shows the results of real-time PCR using, as templates, the genomic DNA extracted from wild-type cells (WT), the genomic DNA extracted from cells having bi-allelic mutations (T4 or T6), and a genomic DNA simulating a mono-allelic mutation (WT+T4), in the presence of crRNA_Target or crRNA_NC instead of the target-specific oligoribonucleotide shown in the preceding figures. crRNA_Target is a crRNA containing an RNA sequence complementary to the CRISPR target site, and crRNA_NC is a control crRNA containing an RNA sequence complementary to an irrelevant locus.

The results are shown in FIG. 7. The pattern of PCR amplification in the presence of crRNA_Target was comparable to those obtained above using THYN1-specific ORNs (see FIGS. 2, 3, and 4). crRNA_NC did not affect amplification of the target nucleic acid region.

Figure 8:
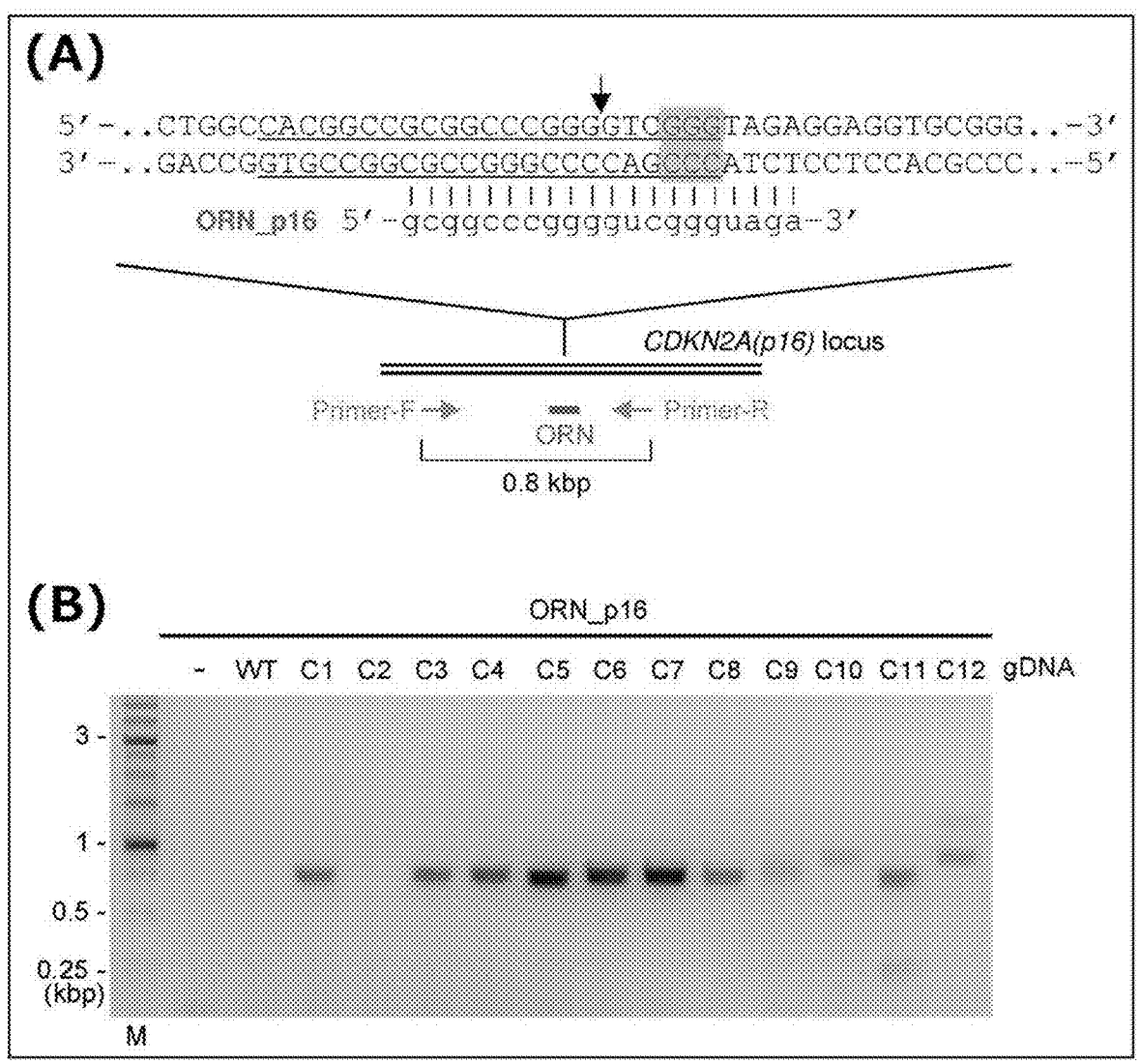
FIG. 8A shows the indicated oligoribonucleotide (ORN_p16, see Table 1) hybridized with the nucleotide sequence of the target nucleic acid region (SEQ ID NO: 37) containing a CRISPR cleavage site in the human CDKN2A (p16) locus; and the region to be amplified using a CDKN2A (p16)-specific primer set.
FIG. 8B shows the results of PCR using the genomic DNAs of 12 clones (C1 to C12) as templates in the presence of ORN_p16. The 12 clones were isolated from a cell population transfected with a CRISPR complex targeting the CDKN2A(p16) locus.

Example 2: Screening for Genome-Edited Cells (2-1) Screening for Human 293T Cells Edited at CDKN2A (p16) Locus We performed CRISPR-mediated genome editing of the CDKN2A(p16) locus in human 293T cells and investigated whether the detection method of the present invention would be applicable to screening for the cells having a mutation in the CDKN2A(p16) locus. FIG. 8A shows the nucleotide sequence of the target nucleic acid region (CTGGC-CACGGCCGCGGCCCGGGGTCGGGTAGAG-GAGGTGCGGG (SEQ ID NO: 37)) containing a CRISPR cleavage site in the human CDKN2A(p16) locus and its complementary sequence; ORN_p16 hybridized with the target nucleic acid region; and the region to be amplified using a CDKN2A(p16)-specific primer set. In the figure, the CRISPR target site (reference sequence) is underlined, PAM is shaded, and the CRISPR cleavage site is shown by an arrow.

CRISPR-mediated genome editing was performed at the CDKN2A(p16) locus in human 293T cells, followed by single-colony isolation. From 12 individual clones (C1 to C12), genomic DNAs were extracted. PCR was performed on these genomic DNAs using a CDKN2A(p16)-specific primer set (hCDKN2A-ORN-F and hCDKN2A-ORN-R, see Table 2) and KOD DNA polymerase (KOD-Plus-Ver. 2) in the presence or absence of ORN_p16.

The results are shown in FIG. 8B. The target nucleic acid region was amplified from 11 of the 12 samples, indicating that genome editing had occurred in the corresponding clones. From the genomic DNAs of C9, C11, and C12, two PCR products per clone were obtained, indicating that genome editing had occurred differently in each allele. The amplified product from C10 had a molecular weight exceeding 1 kb, indicating that an insertion mutation had occurred in this clone. The amplified products from the genomic DNA of C1 and C3 to C8 had the same size (0.8 kbp) as the PCR product obtained by amplification from the wild-type genomic DNA in the absence of the ORN. To characterize the types of the mutations in these clones, the amplified products were subjected to sequencing. As a result, a sequencing signal corresponding to the intact CRISPR target site was not detected in any of the amplified products from C1 and C3 to C8, indicating that bi-allelic mutations had been introduced into the target site in these clones. These results show the detection method of the present invention can be used for screening for genome-edited cells.

(2-2) Screening for Cells Edited at Multiple Target Sites

Genome editing can be used to introduce mutations simultaneously into multiple loci in a single cell. In this study, we investigated whether the detection method of the present invention would be applicable to screening for cells edited at multiple target sites.

CRISPR-mediated genome editing was performed at the CDKN2A(p16) and THYN1 loci in human 293T cells, followed by single-colony isolation. From 11 individual clones (CT1 to CT11), genomic DNAs were extracted. PCR was performed on these genomic DNAs using a CDKN2A (p16)-specific primer set (hCDKN2A-ORN-F and hCDKN2A-ORN-R, see Table 2), a THYN1-specific primer set (hTHYN1-gRNA-target-15-F2, hTHYN1-gRNA-target-15-R2, see Table 2), and KOD DNA polymerase (KOD-Plus-Ver. 2) in the presence of ORN_p16 and ORN_24b or in the absence of ORNs (see FIG. 9A).

Figure 9:
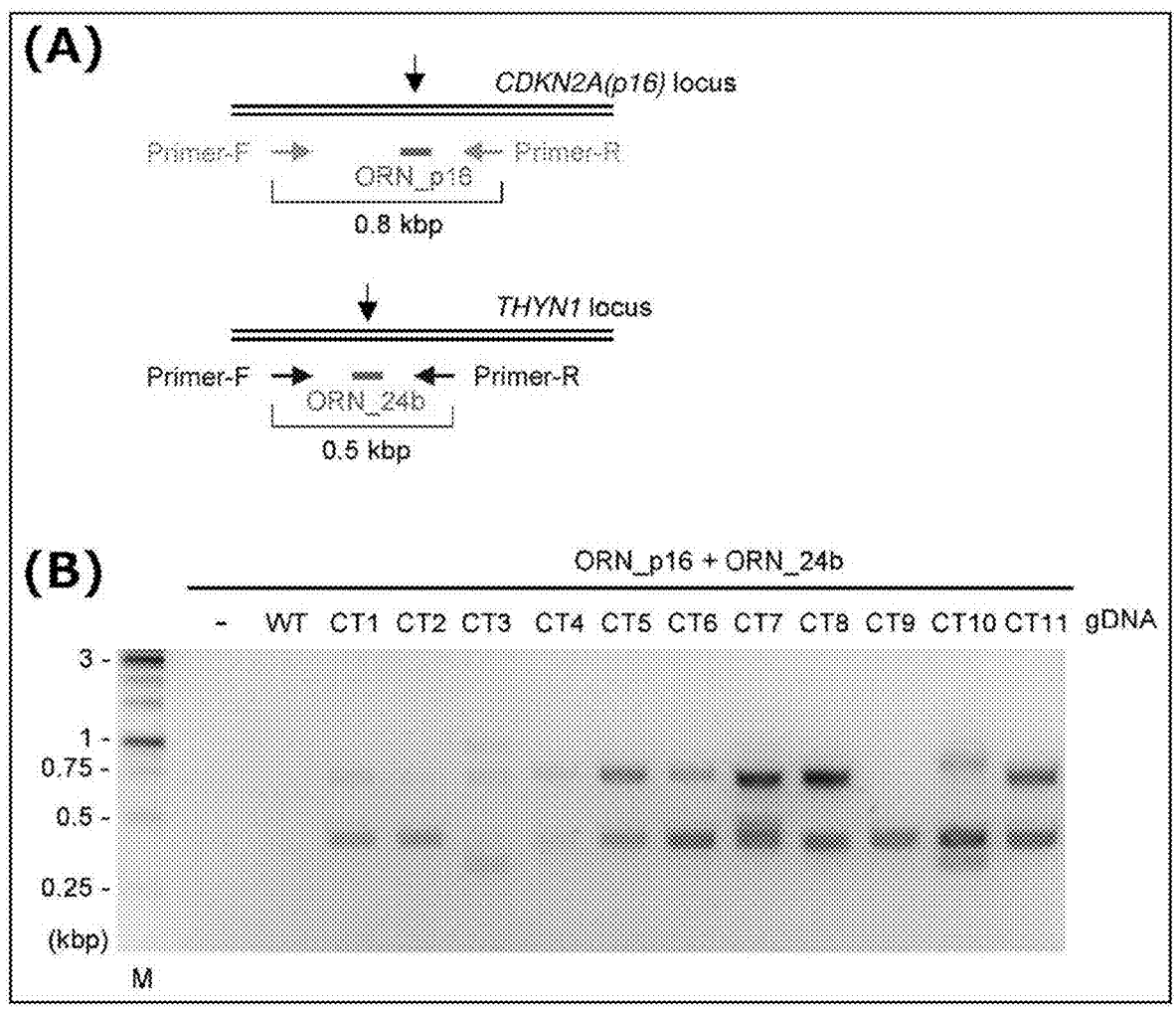
FIG. 9A shows the region to be amplified using a CDKN2A(p16)-specific primer set (top) and the region to be amplified using a THYN1-specific primer set (bottom).
FIG. 9B shows the results of PCR using the genomic DNAs of 11 clones (CT1 to CT11) as templates in the presence of ORN_p16 and ORN_24b. The 11 clones were isolated from a cell population transfected with a CRISPR complex targeting the CDKN2A(p16) locus and a CRISPR complex targeting the THYN1 locus.

The results are shown in FIG. 9B. The amplified product of the CDKN2A(p16) locus was obtained from the genomic DNAs of 9 of the 11 clones (CT1, CT3 to CT8, CT10, and CT11), and the amplified product of the THYN1 locus was obtained from the genomic DNAs of all the 11 clones. This indicates successful genome editing at each locus. The amplified products from CT3, CT7, and CT10 were different in length from those from the other clones, indicating that the target loci in the three clones were mutated mono-allelically or bi-allelically. The other clones were subjected to PCR in the absence of ORNs, and the amplified products were sequenced. As shown in Table 3, CT2 and CT9 had mutations in the THYN1 locus, but not in the CDKN2A (p16) locus, whereas CT1, CT4 to CT8, and CT11 had mutations in both loci. These results show the detection method of the present invention can be used for screening for cells edited at multiple target sites.

TABLE 3

|  |  | CT1 | CT2 | CT4 | CT5 | CT6 | CT8 | CT9 | CT11 |
|---|---|---|---|---|---|---|---|---|---|
| CDKN2A(p16) | DNA sequencing signals of PCR products (Supplementary FIG. S10) | 2 signals | 1 signal | 1 signal (+1 faint signal) | 3 signals | 1 signal | 3 signals | 1 signal | 3 signals |
|  | DNA sequences of the target sites | WT + Mutation | WT | WT (+ Mut) | N.C. | Mutation | N.C. | WT | N.C. |
|  | Types of mutations | 39-bp deletion (mono-allelic) | — | (10-bp deletion) | — | 2-bp detection (bi-allelic, homo) | — | — | — |
| THYN1 | DNA sequencing signals of PCR products (Supplementary FIG. S10) | 2 signals | 3 signals | 3 signals | 1 signal | 3 signals | 2 signals | 3 agents | 2 agents |
|  | DNA sequences of the target sites | Mutation | N.C. | N.C. | Mutation | N.C. | Mutation | N.C. | Mutation |
|  | Types of mutations | 11-bp and 9-bp deletion (bi-allelic) | — | — | 11-bp deletion (bi-allelic, homo) | — | 11-bp deletion (bi-allelic, hetero) | — | 11-bp deletion and 1-bp insertion (bi-allelic) |

Example 3: Detection of Point Mutations

Genome editing can be used to introduce a point mutation, and detection of such a mutation is practically important. We investigated whether the detection method of the present invention would be effective for detecting a point mutation.
(3-1) Detection of 1-Base Deletion Mutation The results of the sequencing of C4 and C6 in the above (2-1) show that these two clones have different mutations in the nucleotide sequence of the target nucleic acid region containing a CRISPR cleavage site in the wild-type human CDKN2A(p16) locus. The nucleotide sequence of the target nucleic acid region is CTGGCCACGGCCGCGGCCCGGGGTCGGGTAGAGGAG GTGCGGG (SEQ ID NO: 38; the CRISPR target site (reference sequence) is underlined, PAM is GGG at positions 26 to 28, and the CRISPR cleavage site is between G at position 22 and G at position 23). The mutations are as follows.
C4: The 6 nucleotides at positions 20 to 25 of the nucleotide sequence of SEQ ID NO: 38 are deleted in one allele, and the nucleotide at position 22 is deleted in the other allele.
C6: The 6 nucleotides at positions 20 to 25 of the nucleotide sequence of SEQ ID NO: 38 are deleted in one allele, and the 2 nucleotides at positions 22 and 23 are deleted in the other allele.

PCR was performed on the genomic DNA extracted from wild-type cells (WT) and the genomic DNA extracted from C4 or C6 cells using a CDKN2A(p16)-specific primer set (hCDKN2A-(–)Bisul-F2 and hCDKN2A-(–)Bisul-R2, see Table 2) and KOD DNA polymerase (KOD-Plus-Ver. 2) in the presence of ORN_p16 in a two-step protocol at an annealing/elongation temperature of 62° C. or 70° C. The results are shown in FIG. 10A. The amplified product was obtained from the C4 or C6 genomic DNA at an annealing/elongation temperature of 62° C. (left) as well as 70° C. (right), but no amplified product was obtained from the WT genomic DNA at either temperature.

Figure 11:
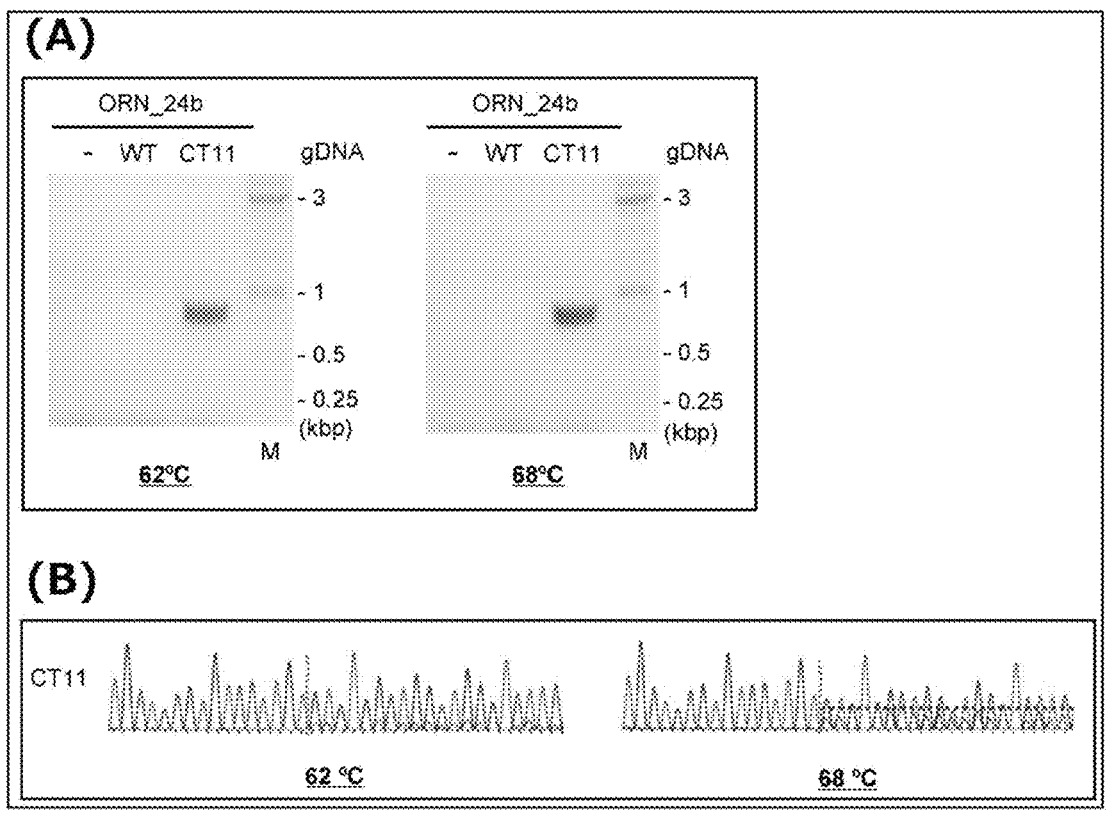
FIG. 11A shows the results of PCR using, as templates, the genomic DNA extracted from cells having a 1-base insertion in one allele (CT11) in the presence of ORN_24b at an annealing temperature of 62° C. or 68° C.
FIG. 11B shows the results of sequencing analysis of the amplified products obtained at the indicated annealing temperatures.

The obtained amplified products were subjected to sequencing. The results are shown in FIG. 10B. In the case of the annealing/elongation temperature of 62° C., two sequencing signals were detected in the amplified product from C6, whereas a single sequencing signal corresponding to the 6-base deleted allele was detected in the amplified product from C4, indicating that amplification of the 1-base deleted allele was inhibited by hybridization with ORN_p16. On the other hand, in the case of the annealing/ elongation temperature of 70° C., a sequencing signal corresponding to the 1-base deleted allele was also detected in the amplified product from C4. These results show that the adjustment of the annealing/elongation temperature for the ORN to be used enables the detection of a 1-base deletion in the reference sequence.
(3-2) Detection of 1-Base Insertion Mutation As shown in the above (2-2), CT11 has a 1-base insertion in one allele of the THYN1 locus (11-base deletion in the other allele, see Table 3). In this study, PCR was performed on the genomic DNA extracted from wild-type cells (WT) and the genomic DNA extracted from CT11 cells using a THYN1-specific primer set (hTHYN1-gRNA-target-15-F5 and hTHYN1-gRNA-target-15-R5, see Table 2) and KOD DNA polymerase (KOD-Plus-Ver. 2) in the presence of ORN_24b at an annealing temperature of 62° C. or 68° C. The results are shown in FIG. 11A. The amplified product was obtained from the CT11 genomic DNA at an annealing temperature of 62° C. (left) as well as 68° C. (right), but no amplified product was obtained from the WT genomic DNA at either temperature.

The obtained amplified products were subjected to sequencing. The results are shown in FIG. 11B. A sequencing signal corresponding to the nucleotide sequence having a 1-base insertion was not detected in the amplified product obtained at the annealing temperature of 62° C., but was detected in the amplified product obtained at the annealing temperature of 68° C. These results show that the adjustment of the annealing temperature for the ORN to be used enables the detection of a 1-base insertion in a target nucleic acid region.
(3-3) Detection of 1-Base Substitution HCT116 cells have a 1-base (G) insertion in one allele of the CDKN2A(p16) locus. We investigated whether the detection method of the present invention would be effective for detecting a mutation using the genomic DNA extracted from HCT116 cells and an ORN hybridizable with the target site having a mutation at one end (ORN_Gx5). As shown in FIG. 12A, the nucleotide sequence CCGCGGCCCGGGGGTCGGGTAGAG- GAGGTGCGGGCG (SEQ ID NO: 39) of the Gx5 allele has an insertion of G between C at position 9 and G at position 10 of the nucleotide sequence CCGCGGCCCGGGGTCGGGTAGAG-GAGGTGCGGGCG (SEQ ID NO: 40) of the Gx4 allele. In the alignment of both the sequences, C at position 9 of the nucleotide sequence of the Gx4 allele can be regarded as being substituted by G in the nucleotide sequence of the Gx5 allele. ORN_Gx5 is completely complementary to the nucleotides at positions 10 to 30 (reference sequence) of the nucleotide sequence of the Gx5 allele. Meanwhile, ORN_Gx5 is completely complementary to the nucleotides at positions 11 to 30 of the nucleotide sequence of the Gx4 allele, but has a mismatch with cytosine (C) at position 10. PCR was performed on the genomic DNA extracted from the HCT116 cells using a CDKN2A(p16)-specific primer set (hCDKN2A-(−)Bisul-F2 and hCDKN2A-(−)Bisul-R2, see Table 2) and KOD DNA polymerase (KOD-Plus-Ver. 2) in the presence of ORN_Gx5 in a two-step protocol at an annealing/elongation temperature of 64° C., 68° C., or 72° C. As a result, the amplified product was not obtained at the annealing/elongation temperature of 64° C., but was obtained at both the annealing/elongation temperatures of 68° C. and 72° C.

The amplified products obtained at the annealing/elongation temperatures of 68° C. and 72° C. were subjected to sequencing. The results are shown in FIG. 12B. The amplified product at the annealing/elongation temperature of 68° C. showed a very weak sequencing signal corresponding to the nucleotide sequence of the Gx5 allele, which had no mismatch with ORN_Gx5, indicating that ORN_Gx5 inhibited amplification. In contrast, the amplified product at the annealing/elongation temperature of 72° C. showed a strong sequencing signal corresponding to the nucleotide sequence of the Gx5 allele, indicating that ORN_Gx5 did not inhibit amplification. These results show that the adjustment of the annealing/elongation temperature for the ORN to be used enables the detection of a 1-base substitution in a target nucleic acid region. Also shown was that a mutation can be detected when the site of the mutation is aligned with not only the center but also the end of the ORN.

Example 4: Examination of Two-Step PCR Conditions (4-1) Inhibition of Two-Step PCR Amplification by Mouse Tax1bp1 Locus-Targeting ORN The ORN used was ORN_Tax (see Table 1).

FIG. 13A shows ORN_Tax hybridized with the nucleotide sequence of the target nucleic acid region (CCATTA-CACCTTAACTCCGTATATCCAT (SEQ ID NO: 41)) in the mouse Tax1bp1 locus; and the region to be amplified using a Tax1bp1-specific primer set.

ORN_Tax, the genomic DNA of Ba/F3 cells, a Tax1bp1-specific primer set (mTax1bp1-exon2-F2, mTax1bp1-exon2-R2, see Table 2), and KOD DNA polymerase (KOD-Plus-Ver.2) were used for two-step PCR at six different annealing/elongation temperatures ranging 50 to 65° C. as shown in FIG. 13B. The results are shown in FIG. 13C. When the genomic DNA extracted from mouse Ba/F3 cells was used for PCR in the absence of the ORN, a 0.6-kbp region was amplified. The addition of 1 μM ORN_Tax to the reaction mixture inhibited amplification at annealing/elongation temperatures of 56° C. or less, and particularly strongly inhibited amplification at annealing/elongation temperatures of 50° C. and 53° C. These results show that the adjustment of the annealing/elongation temperature for the ORN to be used enables specific inhibition of PCR amplification of a target nucleic acid region in a two-step protocol. Also shown was that ORN_Tax1 hybridizes with a template DNA at a temperature of 53 to 56° C.

(4-2) Inhibition of Two-Step PCR Amplification by Human c-FOS Locus-Targeting ORN The ORN used was ORN_FOS (see Table 1).

Figure 14:
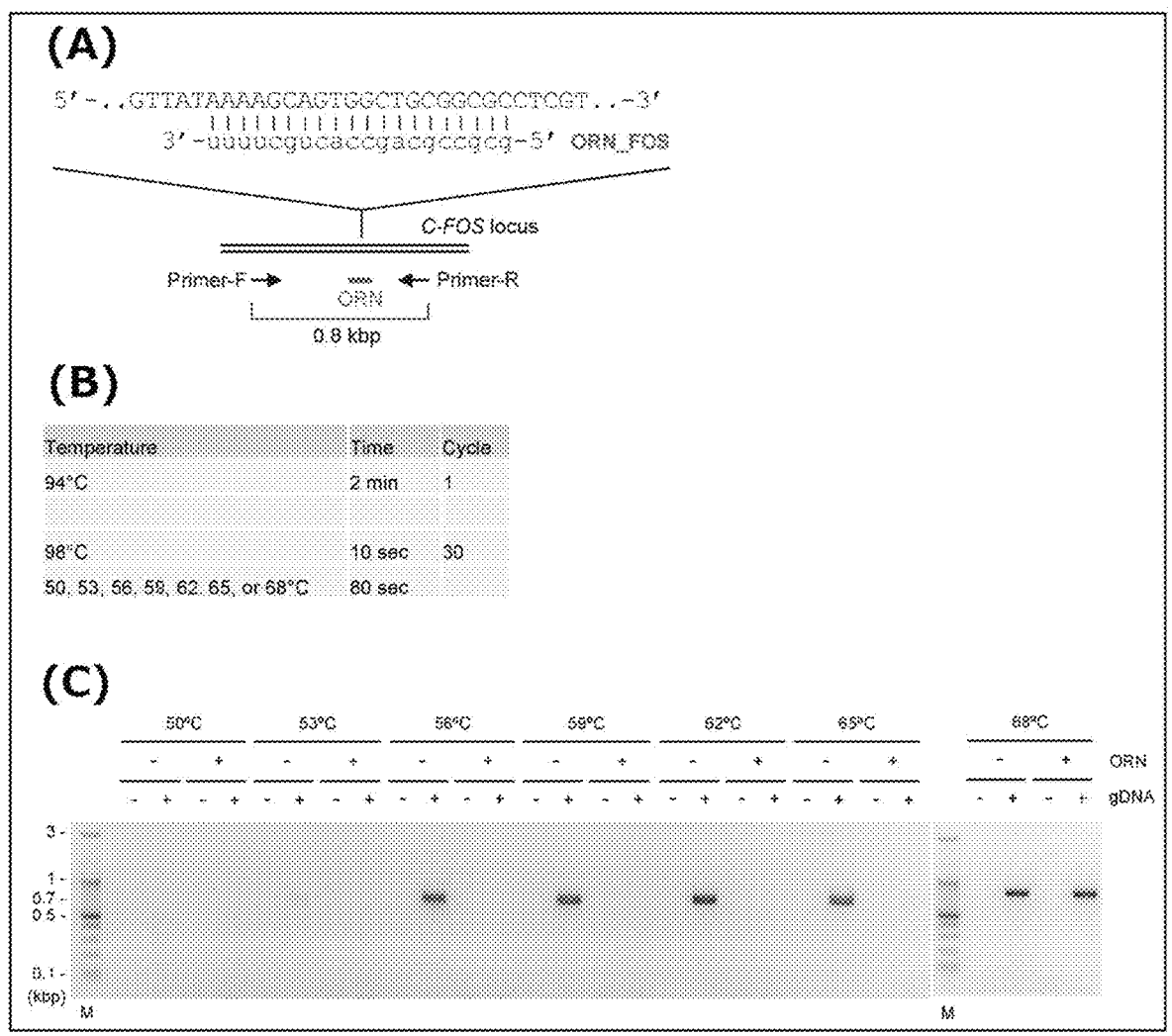
FIG. 14A shows the indicated oligoribonucleotide (ORN_FOS, see Table 1) hybridized with the nucleotide sequence of the target nucleic acid region (SEQ ID NO: 42) in the human c-FOS locus; and the region to be amplified using a c-FOS-specific primer set.
FIG. 14B shows the reaction conditions of two-step PCR.
FIG. 14C shows the results of two-step PCR using, as a template, the wild-type genomic DNA in the presence of ORN_FOS.

FIG. 14A shows ORN_FOS hybridized with the nucleotide sequence of the target nucleic acid region (GT-TATAAAAGCAGTGGCTGCGGCGCCTCGT (SEQ ID NO: 42)) in the human c-FOS locus; and the region to be amplified using a c-FOS-specific primer set.

ORN_FOS, the genomic DNA of 293T cells, a c-FOS-specific primer set (hc-fos-prom-F and hc-fos-prom-R, see Table 2), and KOD DNA polymerase (KOD-Plus-Ver.2) were used for two-step PCR at seven different annealing/elongation temperatures ranging 50 to 68° C. as shown in FIG. 14B. The results are shown in FIG. 14C. When the genomic DNA extracted from human 293T cells was used for PCR in the absence of the ORN, a 0.8-kbp region was specifically amplified at annealing/elongation temperatures of 53 to 68° C. The addition of 1 μM ORN_FOS to the reaction mixture strongly inhibited amplification at annealing/elongation temperatures of 53 to 65° C., but allowed specific amplification of the 0.8-kbp region only at the annealing/elongation temperature of 68° C. These results also show that the adjustment of the annealing/elongation temperature for the ORN to be used enables specific inhibition of PCR amplification of a target nucleic acid region in a two-step protocol. Also shown was that ORN_FOS hybridizes with a template DNA at a temperature of 65 to 68° C.

The Tm value of DNA can be predicted and generally calculated by the following formula:

$Tm=(a+t)\times 2+(g+c)\times 4$ wherein a, t, g, and c indicate the numbers of corresponding bases A, T, G, and C, respectively.

Figure 12:
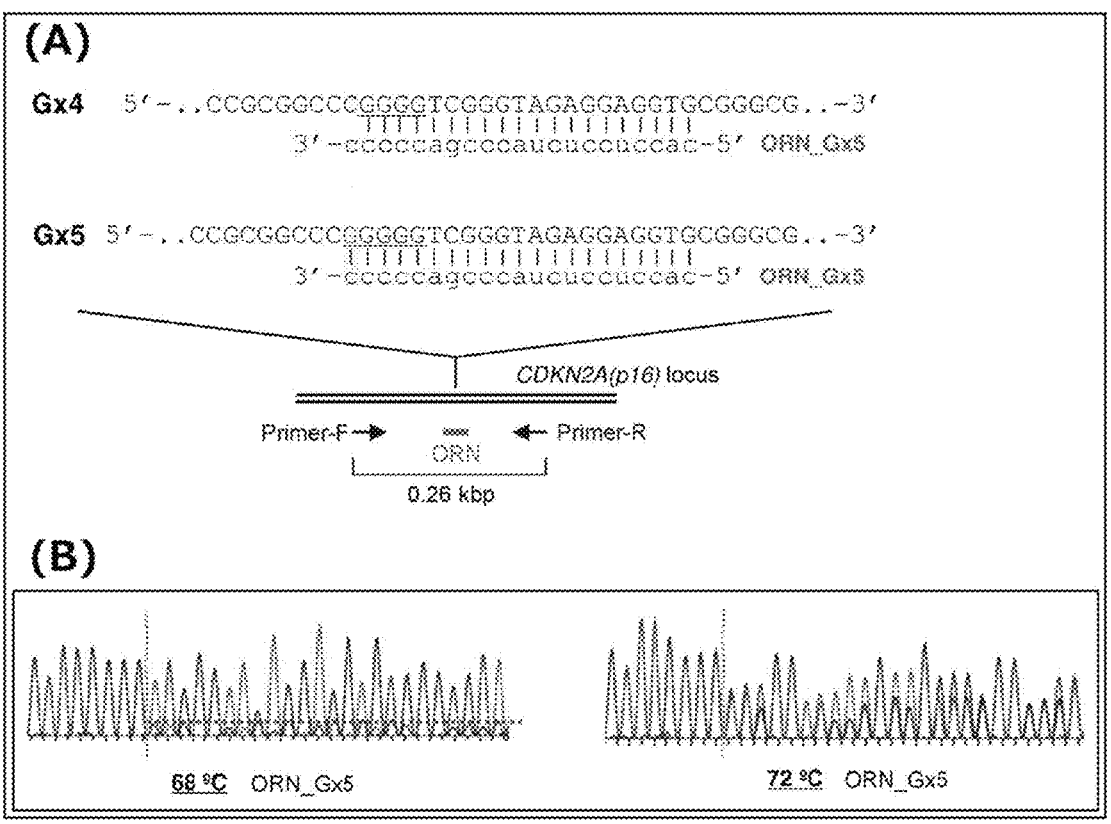
FIG. 12A shows ORN_Gx5 hybridized with the genomic DNA extracted from HCT116 cells having a 1-base (G) insertion in one allele of the CDKN2A(p16) locus (Gx5: SEQ ID NO: 39); and the region to be amplified using a CDKN2A(p16)-specific primer set. The CDKN2A(p16) locus without the 1-base (G) insertion is also shown as Gx4 (SEQ ID NO: 40).
FIG. 12B shows the results of sequencing analysis of the amplified products obtained by two-step PCR at annealing/elongation temperatures of 68° C. and 72° C.
Figure 13:
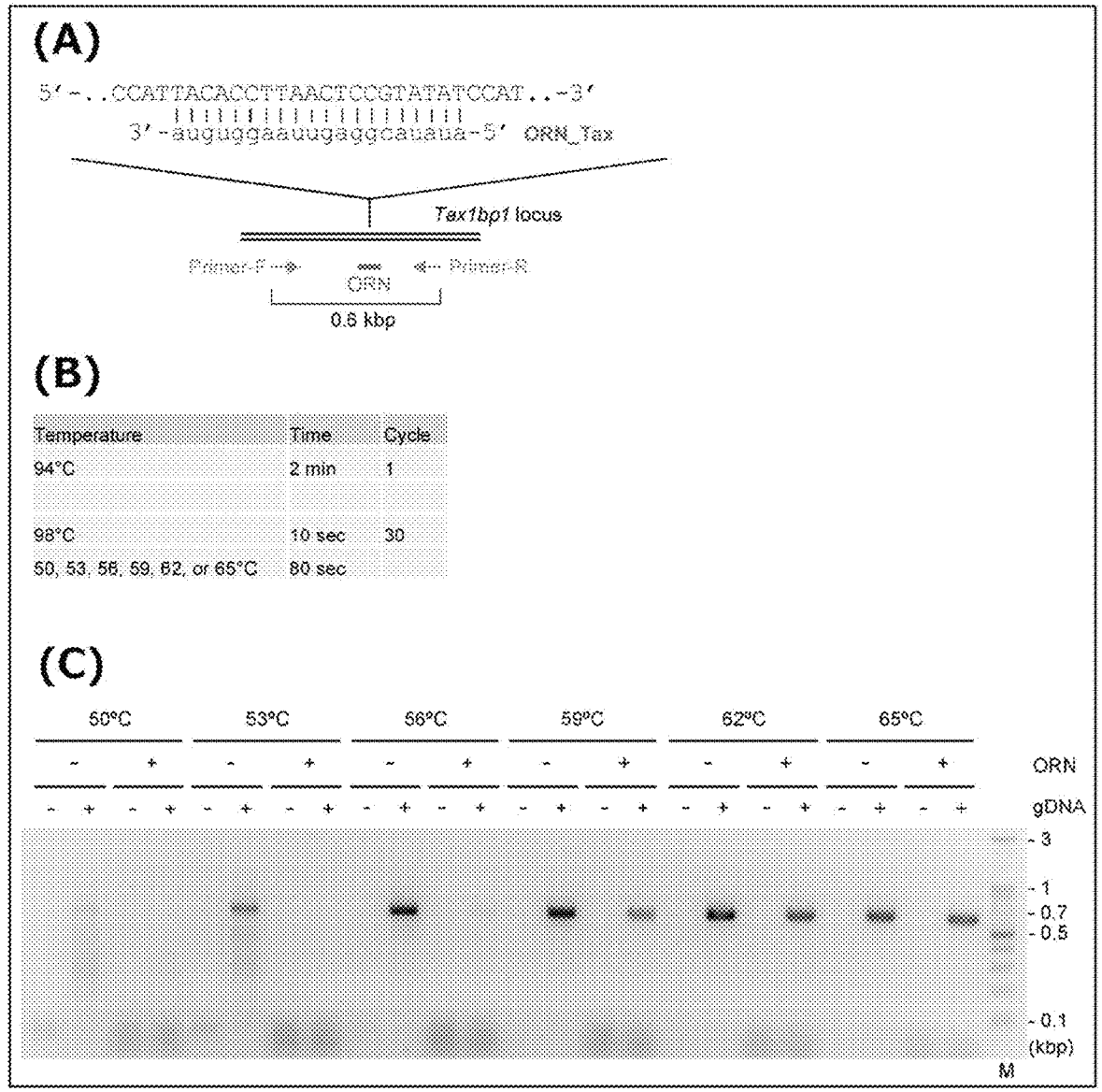
FIG. 13A shows the indicated oligoribonucleotide (ORN_Tax, see Table 1) hybridized with the nucleotide sequence of the target nucleic acid region (SEQ ID NO: 41) in the mouse Tax1bp1 locus; and the region to be amplified using a Tax1bp1-specific primer set.
FIG. 13B shows the reaction conditions of two-step PCR.
FIG. 13C shows the results of two-step PCR using, as a template, the wild-type genomic DNA in the presence of ORN_Tax.

The Tm values of ORN_Tax and ORN_FOS were calculated by the above formula with the replacement of base T by U. The calculated Tm values of ORN_Tax and ORN_FOS were 54° C. and 66° C., respectively (Table 4). The actual Tm value of ORN_Tax was 53 to 56° C. as shown in the results of FIG. 12, and the actual Tm value of ORN_Tax was 65 to 68° C. as shown in the results of FIG. 13. These results show that the Tm values of ORNs can be predicted.

TABLE 4

| Name | Sequence (5' → 3') | Target locus | Length (bases) | GC % | Tm |
|---|---|---|---|---|---|
| ORN_Tax | auauacggaguuaaggugua | mouse Tax1bp1 | 20 | 35 | 54 |
| ORN_FOS | gcgccgcagccacugcuuuu | human c-FOS | 20 | 65 | 66 |

The Tm value is calculated by the following formula: Tm = (a + u) × 2 + (g + c) × 4 wherein a, u, g, and c indicate the numbers of corresponding bases A, U, G, and C, respectively.

Figure 15:
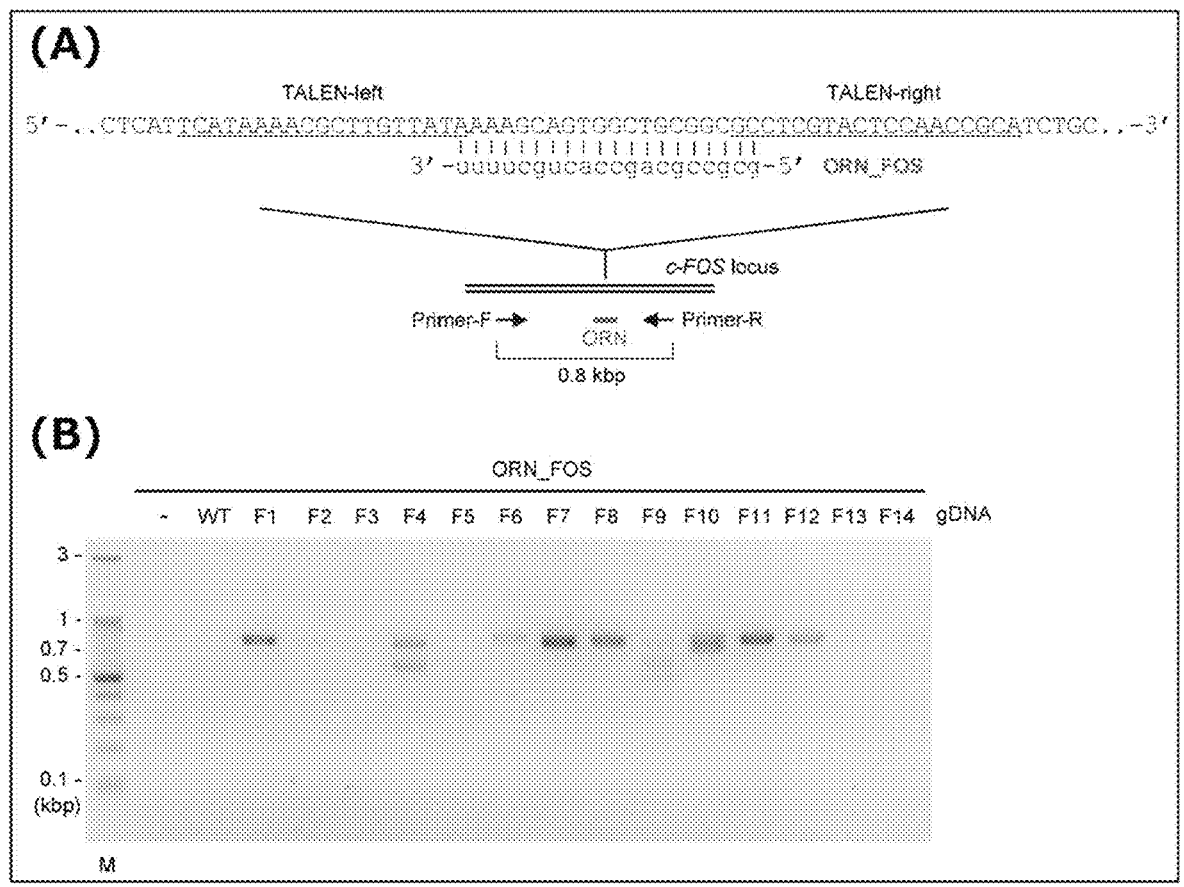
FIG. 15A shows the indicated oligoribonucleotide (ORN_FOS, see Table 1) hybridized with the nucleotide sequence of the target nucleic acid region (SEQ ID NO: 43) containing a TALEN cleavage site in the human c-FOS locus; and the region to be amplified using a c-FOS-specific primer set.
FIG. 15B shows the results of two-step PCR using the genomic DNAs of 14 clones (F1 to F14) as templates in the presence of ORN_FOS. The 14 clones were isolated from a cell population transfected with a TALEN pair targeting the c-FOS locus.

Example 5: Screening for Genome-Edited Cells by Two-Step PCR (5-1) Screening for Human 293T Cells Edited at c-FOS Locus We performed TALEN-mediated genome editing of the c-FOS locus in human 293T cells and investigated whether the detection method of the present invention would be applicable to screening for the cells having a mutation in the c-FOS locus. FIG. 15A shows the nucleotide sequence of the target nucleic acid region (CTCATTCATAAAACGCTTGT-TATAAAAGCAGTGGCTGCGGCGCCTCGTACTC-CAACCG CATCTGC (SEQ ID NO: 43)) containing a TALEN cleavage site in the human c-FOS locus; ORN_FOS hybridized with the target nucleic acid region; and the region to be amplified using a c-FOS-specific primer set. In the figure, the target sites of TALEN-left and TALEN-right are underlined, and the region flanked by TALEN-left and TALEN-right is targeted for cleavage.

TALEN-mediated genome editing was performed at the c-FOS locus in human 293T cells, followed by single-colony isolation. From 14 individual clones (F1 to C14), genomic DNAs were extracted. PCR was performed on these genomic DNAs using a c-FOS-specific primer set (hc-fos-prom-F and hc-fos-prom-R, see Table 2) and KOD DNA polymerase (KOD-Plus-Ver. 2) in the presence of ORN_FOS in a two-step protocol at an annealing/elongation temperature of 65° C.

Figure 16:
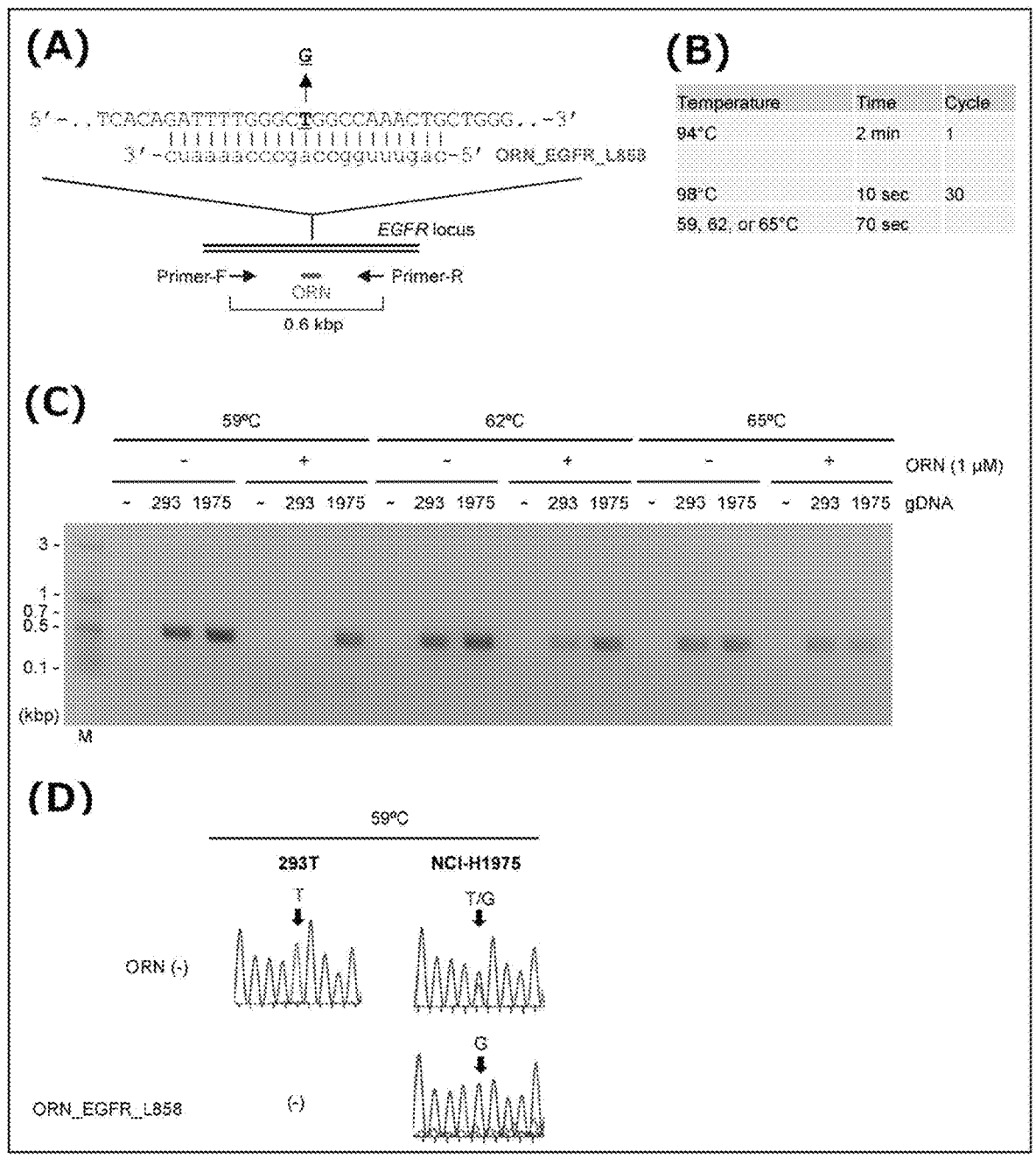
FIG. 16A shows the indicated oligoribonucleotide (ORN_EGFR_L858, see Table 1) hybridized with the nucleotide sequence of the target nucleic acid region (SEQ ID NO: 44) in the human EGFR locus; and the region to be amplified using an EGFR-specific primer set.
FIG. 16B shows the reaction conditions of two-step PCR.
FIG. 16C shows the results of two-step PCR using, as a template, the 293T or NCI-H1975 genomic DNA in the presence of ORN_EGFR_L858.
FIG. 16D shows the results of sequencing analysis of the amplified products obtained at an annealing/elongation temperature of 59° C.

The results are shown in FIG. 15B. The band of the amplified product was clearly observed in 9 of the 14 samples, indicating that genome editing had occurred in the corresponding clones. From the genomic DNAs of F4 and F10, two PCR products per clone were obtained, indicating that genome editing had occurred differently in each allele. From the genomic DNA of F9, three PCR products were obtained, indicating that different types of genome-edited cells were mixed in this clone. To determine the presence or absence of a mutation and characterize the type of the mutation in each of the obtained clones except for F4 and F9, PCR amplification was performed in the absence of the ORN, and the PCR products were subjected to sequencing. As a result, clones F2, F3, F5, F13 and F14, for which no clear band was detected after the previous PCR amplification in the presence of the ORN, had no mutation in the TALEN target site. For the other clones, for which a clear band was detected after the previous PCR amplification in the presence of the ORN, a sequencing signal(s) corresponding to the mutated TALEN target site was detected, indicating that these clones had a mono-allelic mutation or bi-allelic mutations in the target site. The results are summarized in Table 5. Taken together, the above findings show the detection method of the present invention using two-step PCR can be used for screening for genome-edited cells.

the intact nucleotide sequence TCACAGAT-TTTGGGCTGGCCAAACTGCTGGG (SEQ ID NO: 44) in one allele. ORN_EGFR_L858 is completely complementary to the nucleotides at positions 6 to 26 (reference sequence) of the intact nucleotide sequence, but has a mismatch with guanine (G) at position 16 of the 1-base substituted nucleotide sequence. Genomic DNAs were extracted from NCI-H1975 cells and 293T cells, which are free from a 1-base substitution mutation at the corresponding position. PCR was performed on these genomic DNAs using an EGFR-specific primer set (hEGFR-Exon21-F and hEGFR-Exon21-R, see Table 2) and KOD DNA polymerase (KOD-Plus-Ver. 2) in the presence or absence of ORN_EGFR_L858 in a two-step protocol at three different annealing/elongation temperatures ranging 59 to 65° C. as shown in FIG. 16B. As shown in FIG. 16C, the amplified product was obtained from both the genomic DNAs in the absence of ORN_EGFR_L858 regardless of the annealing/elongation temperature. In the presence of ORN_EGFR_L858, no amplified product was obtained from the genomic DNA of 293T cells at the annealing/elongation temperature of 59° C., whereas the amplified product was obtained from the genomic DNA of NCI-H1975 cells at the same annealing/elongation temperature.

The amplified products obtained at the annealing/elongation temperature of 59° C. were subjected to sequencing. The results are shown in FIG. 16D. A sequencing signal corresponding to the intact nucleotide sequence was detected in the amplified product obtained from the genomic DNA of 293T cells in the absence of the ORN. On the other hand, sequencing signals corresponding to both the intact nucleotide sequence and the mutated nucleotide sequence having a 1-base substitution were detected in the amplified product obtained from the genomic DNA of NCI-H1975 cells in the absence of the ORN. In the amplified product obtained from the genomic DNA of NCI-H1975 cells in the presence of ORN_EGFR_L858, only a sequencing signal corresponding to the mutated nucleotide sequence having a 1-base substitution was detected. These results show the detection method of the present invention using two-step PCR enables the detection of a 1-base substitution mutation in a target nucleic acid region.

TABLE 5

| | F1 | F2 | F3 | F5 | F6 | F7 | F8 | F10 | F11 | F12 | F13 | F14 |
|---|---|---|---|---|---|---|---|---|---|---|---|---|
| DNA sequencing signals of PCR products (Supplementary FIG. S10) | 3 signals | 1 signal | 1 signal | 1 signal | 1 signal (+1 faint signal) | 2 signals | 2 signals | 3 signals | 2 signals | 2 signals | 1 signal | 1 signal |
| DNA sequences of the target sites | WT + α | WT | WT | WT | WT + α | Mutation | Mutation | WT + α | Mutation | Mutation | WT | WT |
| Types of mutation | N.C. | — | — | — | N.C. | 9-bp and 12-bp deletion (bi-allelic) | 9-bp deletion (mono-allelic) | N.C. | 1-bp deletion (mono-allelic) | 1-bp insertion (mono-allelic) | — | — |

Example 6: Detection of 1-Base Substitution Mutation by Two-Step PCR (6-1) Detection of 1-Base Substitution Mutation in EGFR Locus in Human NCI-H1975 Cells NCI-H1975 cells have a 1-base substitution mutation in one allele of the EGFR locus. As shown in FIG. 16A, NCI-H1975 cells have a T to G substitution at position 16 of Example 7: Amplification of Genome-Edited Nucleotide Sequences (7-1) Amplification of Genome-Edited Nucleotide Sequences in Human THYN1 Locus We investigated whether the detection method of the present invention using a DNA extracted from a genome-edited cell pool would enable selective amplification of nucleotide sequences each having a mutation in a target nucleic acid region.

For genome editing of the human THYN1 locus, HCT116 cells (4×10⁵ cells) were transfected with a Cas9 expression plasmid (4 μg) and an sgRNA expression plasmid targeting the human THYN1 locus (4 μg) using Lipofectamine 3000 (Thermo Fisher Scientific). Three days later, genomic DNA was extracted from the cells using Quick-DNA Universal Kit (Zymo Research).

For PCR targeting the human THYN1 locus, a PCR reaction mixture containing 20 ng of the HCT116 genomic DNA, 0.3 μM each primer, and 0.5 μM ORN was prepared in a 10 μL volume. The reaction was carried out with an initial denaturation at 94° C. for 2 min, followed by 34 cycles of the following 2 steps: 98° C. for 10 sec, and 68° C. for 90 sec.

The PCR products were electrophoresed on a 1% agarose gel, and if necessary, subjected to sequencing or to cloning into pCR4-TOPO (Thermo Fisher Scientific) and subsequent sequencing. DNA sequencing data were analyzed using Applied Biosystems Sequence Scanner Software v2.0 (Thermo Fisher Scientific).

Figure 17:
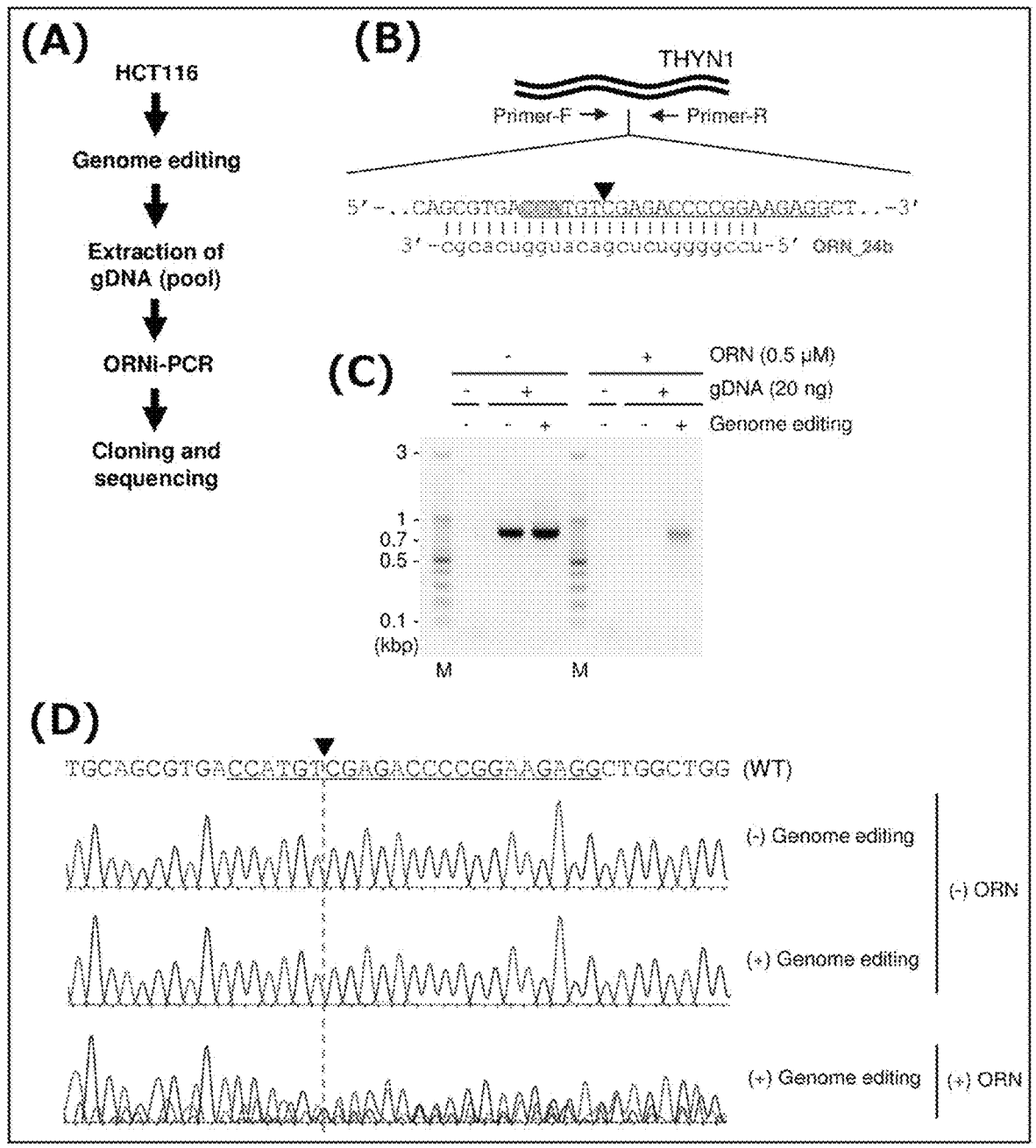
FIG. 17A shows the experiment scheme of Example 7 (7-1).
FIG. 17B shows the indicated oligoribonucleotide (ORN_24b, see Table 1) hybridized with the nucleotide sequence of the target nucleic acid region (SEQ ID NO: 51) in the human THYN1 locus.
FIG. 17C shows the results of two-step PCR using, as templates, the genomic DNA of wild-type cells and the genomic DNA of a genome-edited cell pool in the presence of ORN_24b.
FIG. 17D shows the results of sequencing analysis of the amplified products and the wild-type nucleotide sequence of the human THYN1 locus (SEO ID NO: 52).

The experimental scheme is shown in FIG. 17A. CRISPR-mediated genome editing was performed at the THYN1 locus in HCT116 cells without subsequent cloning. Genomic DNA was extracted from the whole cell population. PCR was performed on the extracted genomic DNA using a THYN1-specific primer set (hTHYN1-gRNA-target-15-F5 and hTHYN1-gRNA-target-15-R5, see Table 2) and KOD DNA polymerase (KOD-Plus-Ver. 2) in the presence or absence of ORN_24b (see Table 1).

FIG. 17B shows ORN_24b hybridized with the nucleotide sequence of the target nucleic acid region (CAGCGTGAC-CATGTCGAGACCCCGGAAGAGGCT (SEQ ID NO: 51)) containing a CRISPR cleavage site in the human THYN1 locus. In the figure, the CRISPR target site (reference sequence) is underlined, PAM is shaded, and the CRISPR cleavage site is shown by an arrow.

The results are shown in FIG. 17C. In the absence of ORN_24b, the target nucleic acid region was amplified from the genomic DNAs of the wild-type cells and the genome-edited cell pool. In the presence of ORN_24b, amplification from the genomic DNA of the wild-type cells was completely inhibited, whereas amplification from the genome-edited cell pool was not completely inhibited. In addition, the PCR products obtained in the absence of ORN_24b and the PCR products obtained in the presence of ORN_24b were subjected to sequencing. As a result, only a sequencing signal corresponding to the wild-type nucleotide sequence (TGCAGCGTGACCATGTCGAGACCCCG-GAAGAGGCTGGCTGG: SEQ ID NO: 52) was detected in the PCR products obtained in the absence of ORN_24b, whereas multiple sequencing signals were detected in the PCR products obtained in the presence of ORN_24b (see FIG. 17D). In the PCR products obtained in the presence of ORN_24, no sequencing signal corresponding to the wild-type nucleotide sequence was detected. This means that ORN 24b inhibits amplification of the THYN1 locus from the genomic DNA of wild-type cells contained in the genome-edited cell pool, but does not affect amplification from the genomic DNAs of genome-edited cells contained in the genome-edited cell pool.

Next, the PCR products obtained in the absence of ORN_24b and the PCR products obtained in the presence of ORN_24b were cloned into plasmids, and the obtained clones were subjected to sequencing. The results are summarized in Table 6. In the case of cloning of the PCR products obtained in the absence of ORN_24b, 2 of 11 clones had a genome-edited nucleotide sequence. In the case of cloning of the PCR products obtained in the presence of ORN_24b, all seven clones had a genome-edited nucleotide sequence. The above results show that PCR performed in a reaction mixture containing an ORN capable of hybridizing with the reference sequence in a target nucleic acid region is effective for inhibiting amplification of a wild-type nucleic acid sequence having no mutation in the target nucleic acid region (reference sequence) and amplifying a mutated nucleic acid sequence having a mutation in the target nucleic acid region (variant sequence).

TABLE 6

|  | Sequenced clones (Total) | Wild-type | Insertion | Deletion |
| --- | --- | --- | --- | --- |
| Genome edited (−ORN) | 11 | 9 | 1 | 1 |
| Genome edited (+ORN) | 7 | 0 | 0 | 7 |

(7-2) Amplification of Genome-Edited Nucleotide Sequences in Human CDKN2A(p16) Locus We conducted another investigation similar to the above (7-1) using the human CDKN2A(p16) locus and crRNA in place of the target-specific ORN.

For genome editing of the human CDKN2A(p16) locus, HCT116 cells (4×10⁵ cells) were transfected with a Cas9 expression plasmid (4 μg) and an sgRNA expression plasmid targeting the human CDKN2A(p16) locus (4 μg) using Lipofectamine 3000 (Thermo Fisher Scientific). Three days later, genomic DNA was extracted from the cells using Quick-DNA Universal Kit (Zymo Research).

For PCR targeting the human CDKN2A(p16) locus, a PCR reaction mixture containing 20 ng of the HCT116 cell genomic DNA, 0.3 μM each primer, and 0.25 μM crRNA was prepared in a 10 μL volume. The reaction was carried out with an initial denaturation at 94° C. for 2 min, followed by 34 cycles of the following 2 steps: 98° C. for 10 sec, and 74° C. for 70 sec.

The PCR products were electrophoresed on a 1% agarose gel, and if necessary, subjected to sequencing. DNA sequencing data were analyzed using Applied Biosystems Sequence Scanner Software v2.0 (Thermo Fisher Scientific).

In the same manner as in the experimental scheme shown in FIG. 17A, CRISPR-mediated genome editing was performed at the human CDKN2A(p16) locus in HCT116 cells without subsequent cloning. Genomic DNA was extracted from the whole cell population. PCR was performed on the extracted genomic DNA using a human CDKN2A(p16)-specific primer set (hCDKN2A-CpG-645-F and hCDKN2A-CpG-645-R) and KOD DNA polymerase (KOD-Plus-Ver. 2) in the presence or absence of crRNA_lef5.

```
hCDEN2A-CpG-645-F:
                                        (SEQ ID NO. 45)
ggagacccaacctgqqgcqacttca hCDKN2A-CpG-645-R:
                                        (SEQ ID NO: 46)
ctgtacgcgcgtggctcctcattcc
```

```
crRNA_lef5:
                                        (SEQ ID NO: 47)
ugggcggaccgcgugcgcuguuuuagagcuaugcuguuu
```

Figure 18:
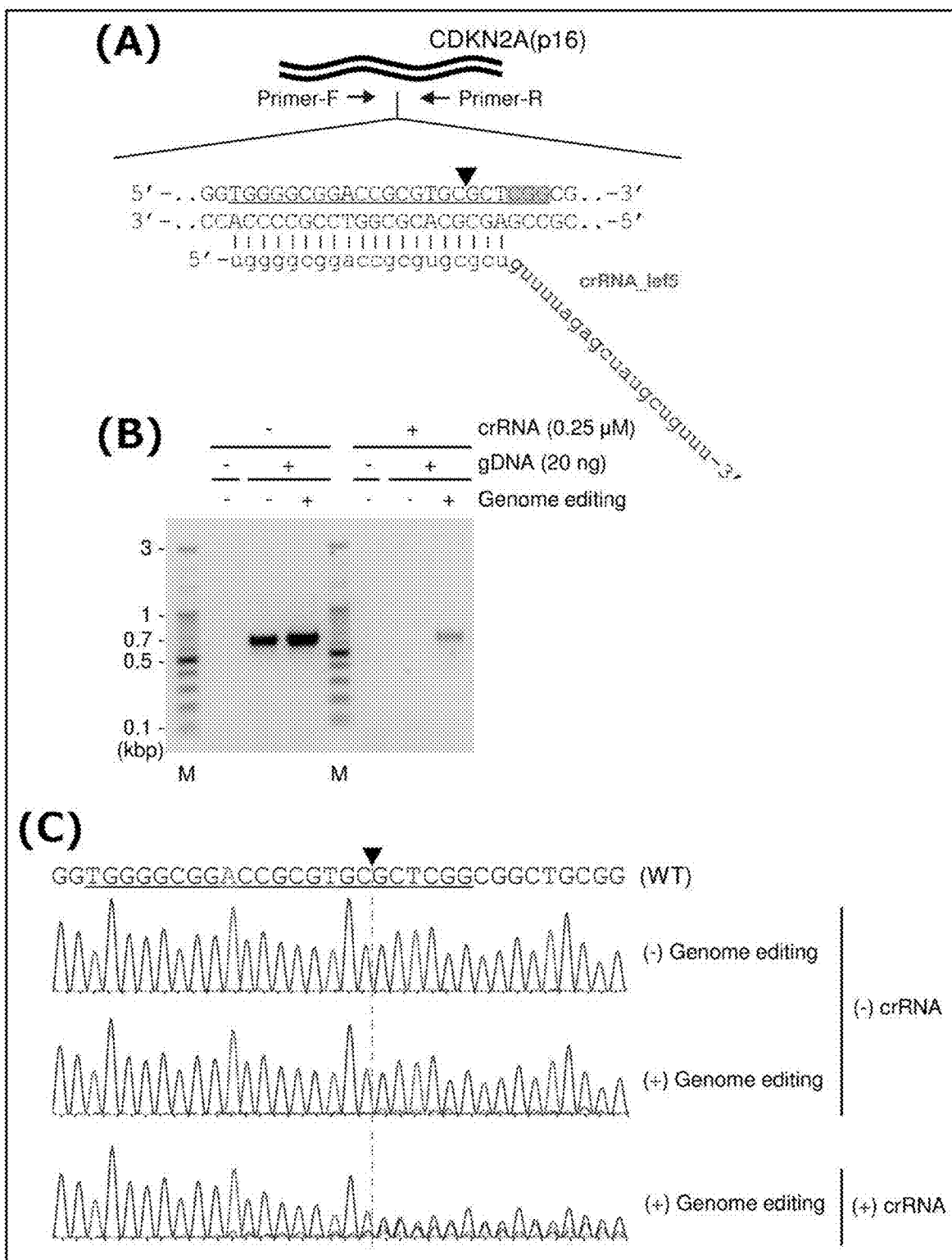
FIG. 18A shows the indicated crRNA (crRNA_lef5, SEQ ID NO: 47) hybridized with the nucleotide sequence of the target nucleic acid region (SEQ ID NO: 53) in the human CDKN2A(p16) locus.
FIG. 18B shows the results of two-step PCR using, as templates, the genomic DNA of wild-type cells and the genomic DNA of a genome-edited cell pool in the presence of crRNA_lef5.
FIG. 18C shows the results of sequencing analysis of the amplified products.

FIG. 18A shows the nucleotide sequence of the target nucleic acid region (GGTGGGGCGGACCGCGTGCGCTCGGCG (SEQ ID NO: 53)) containing a CRISPR cleavage site in the human CDKN2A(p16) locus and its complementary sequence; and crRNA_lef5 hybridized with the target nucleic acid region. In the figure, the CRISPR target site (reference sequence) is underlined, PAM is shaded, and the CRISPR cleavage site is shown by an arrow.

The results are shown in FIG. 18B. In the absence of crRNA, the target nucleic acid region was amplified from the genomic DNAs of the wild-type cells and the genome-edited cell pool. In the presence of crRNA_lef5, amplification from the genomic DNA of the wild-type cells was completely inhibited, whereas amplification from the genome-edited cell pool was not completely inhibited. Next, the PCR products obtained in the absence of crRNA_lef5 and the PCR products obtained in the presence of crRNA_lef5 were subjected to sequencing. As a result, a sequencing signal corresponding to the wild-type nucleotide sequence (GGTGGGGCGGACCGCGTGCGCTCGGCGGCTGCGG: SEQ ID NO: 54) was mainly detected in the PCR products obtained in the absence of crRNA_lef5, whereas multiple sequencing signals were detected in the PCR products obtained in the presence of crRNA_lef5 (see FIG. 18C). This means that crRNA_lef5 inhibits amplification of the CDKN2A(p16) locus from the genomic DNA of wild-type cells contained in the genome-edited cell pool, but does not affect amplification from the genomic DNAs of genome-edited cells contained in the genome-edited cell pool. The above results show that PCR performed in a reaction mixture containing a crRNA capable of hybridizing with the reference sequence in a target nucleic acid region is effective for inhibiting amplification of a wild-type nucleic acid sequence having no mutation in the target nucleic acid region (reference sequence) and amplifying a mutated nucleic acid sequence having a mutation in the target nucleic acid region (variant sequence).

To summarize the above, the detection method of the present invention can enrich a nucleic acid having a mutated nucleic acid sequence having a mutation in the target nucleic acid region (variant sequence), thus enabling a more efficient analysis of mutational patterns; and also can be used to determine the presence or absence of genome-edited cells contained in a cell population subjected to genome editing. In place of the cloning and sequencing analysis described above, PCR products may be subjected to next-generation sequencing analysis.

Example 8: Amplification of Methylated Cytosine-Containing DNA Region after Bisulfite Treatment (8-1) Amplification of Methylated Cytosine-Containing Human CDKN2A(p16) Locus after Bisulfite Treatment CpG islands are regions with a high frequency of CpG sites, and cytosines in CpG sites can be methylated. Bisulfite treatment converts unmethylated cytosines to uracils but leaves methylated cytosines unchanged. For this reason, in PCR products from a bisulfite-converted DNA, unmethylated cytosines are substituted by thymines, and methylated cytosines remain cytosines. In other words, a bisulfite-converted DNA has a nucleotide sequence different from the original one due to the methylation status of cytosines in CpG sites. In this view, the detection method of the present invention would enable specific amplification of the nucleotide sequence of a DNA region with (or without) methylated cytosines in CpG sites.

In HCT116 cells, CpG methylation in the CpG island is known to occur in only one allele of the human CDKN2A (p16) locus. In this study, the detection method of the present invention after bisulfite conversion of a DNA extracted from HCT116 cells would enable specific amplification of the nucleotide sequence of a DNA region with methylated cytosines in CpG sites in the CpG island of the CDKN2A (p16) locus.

Genomic DNA was extracted from HCT116 cells and subjected to bisulfite treatment using EZ DNA Methylation-Lightning Kit (Zymo Research). For PCR targeting the human CDKN2A(p16) locus, a PCR reaction mixture containing 1 μL of the bisulfite-converted genomic DNA from HCT116 cells, 0.3 μM each primer, and 1 μM ORN was prepared in a 10 μL volume. The reaction was carried out with an initial denaturation at 94° C. for 2 min, followed by 35 cycles of the following 2 steps: 98° C. for 10 sec, and 56° C. for 60 sec. The PCR products were electrophoresed on a 2% agarose gel, and if necessary, subjected to sequencing. DNA sequencing data were analyzed using Applied Biosystems Sequence Scanner Software v2.0 (Thermo Fisher Scientific).

Figure 19:
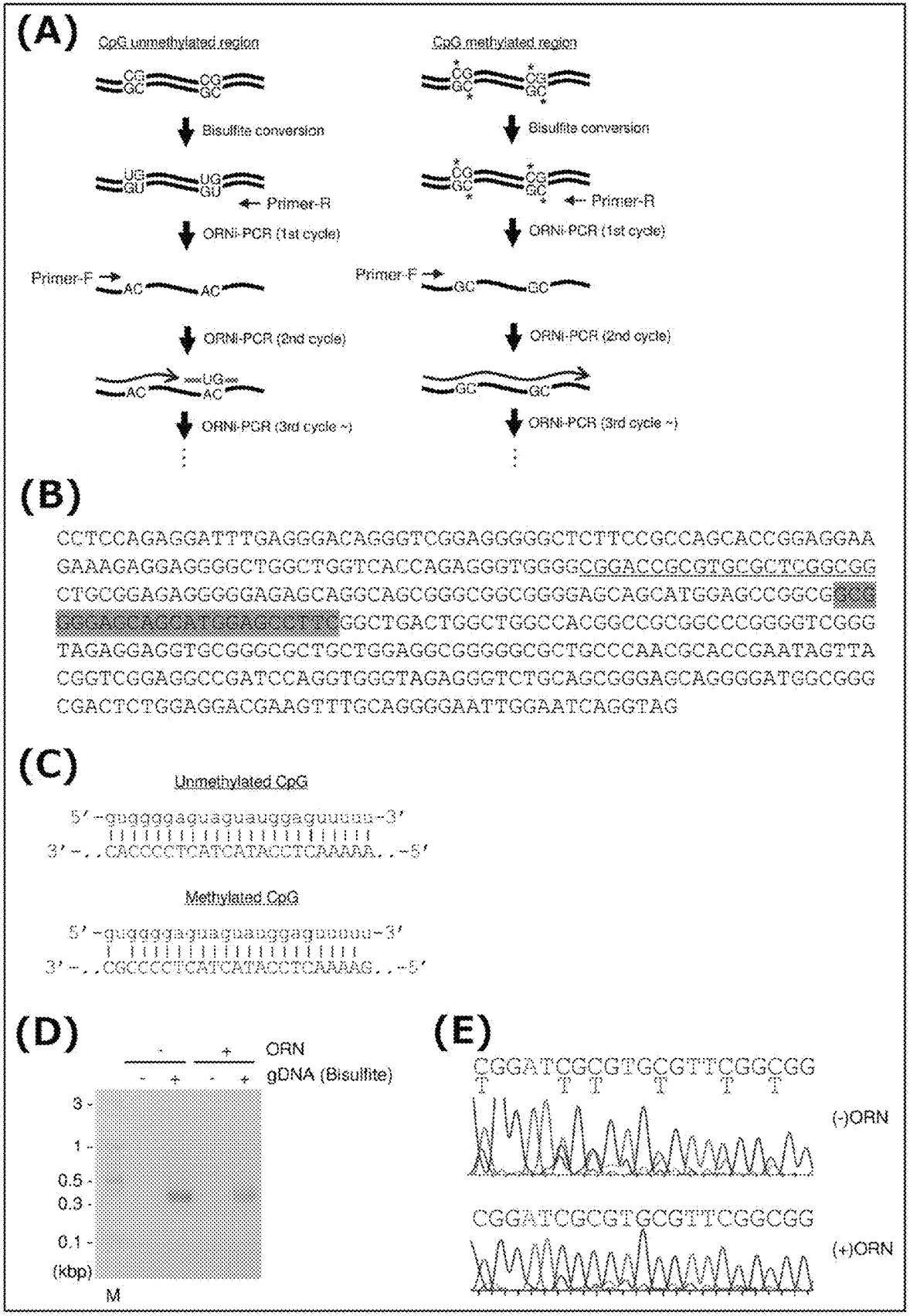
FIG. 19A is a schematic view of the procedure of the detection method of the present invention using a bisulfite-converted DNA as a template.
FIG. 19B shows the nucleotide sequence of a specific DNA region (SEQ ID NO: 55) before bisulfite conversion. The specific DNA region is to be amplified from a bisulfite-converted genomic DNA of HCT116 cells as a template using a CDKN2A(p16)-specific primer set (hCDKN2A-Bisul-CpG-free-F (SEQ ID NO: 48) and hCDKN2A-Bisul-CpG-free-R (SEQ ID NO: 49)).
FIG. 19C shows ORN_hCDKN2A_U (SEQ ID NO: 50) hybridized with the complementary sequence of the shaded region in FIG. 19B after bisulfite conversion (without methylated cytosines (top), and with methylated cytosines (bottom)).
FIG. 19D shows the results of two-step PCR using, as a template, the bisulfite-converted genomic DNA in the presence of ORN_hCDKN2A_U.
FIG. 19E shows the results of sequencing analysis of the amplified products (the underlined region of the sequence in FIG. 19B).

FIG. 19A is a schematic view of the procedure of the detection method of the present invention using a bisulfite-converted DNA as a template. PCR was performed on the bisulfite-converted genomic DNA from HCT116 cells using a CDKN2A(p16)-specific primer set (hCDKN2A-Bisul-CpG-free-F and hCDKN2A-Bisul-CpG-free-R) and KOD-Multi & Epi-(Toyobo) in the presence or absence of ORN_hCDKN2A_U.

```
hCDYN2A-Bisul-CpG-free-F:
                                        (SEQ ID NO: 48)
tttttagaggatttgagggatagg hCDYN2A-Bisul-CpG-free-R:
                                        (SEQ ID NO: 49)
ctacctaattccaattcccctacaaacttc ORN_hCDKN2A_U:
                                        (SEQ ID NO: 50)
guggggaguaguauggaquuuuu
```

FIG. 19B shows the nucleotide sequence of a specific DNA region (SEQ ID NO: 55) before bisulfite conversion. The specific DNA region is to be amplified from the bisulfite-converted genomic DNA of HCT116 cells as a template using the above CDKN2A(p16)-specific primer set. FIG. 19C shows ORN_hCDKN2A_U hybridized with the complementary sequence of the shaded region in FIG. 19B after bisulfite conversion. The top panel shows the case where the shaded region in FIG. 19B does not contain methylated cytosines. The bottom panel shows the case where the shaded region in FIG. 19B contains methylated cytosines. In the case where the shaded region in FIG. 19B does not contain methylated cytosines, ORN_hCDKN2A_U is completely complementary to the complementary sequence (AAAAACTCCATACTACTCCCCAC: SEQ ID NO: 56) of the shaded region. On the other hand, in the case where the shaded region in FIG. 19B contains methylated cytosines, ORN_hCDKN2A_U has a 2-base mismatch to the complementary sequence (GAAAACTCCATAC-TACTCCCCGC: SEQ ID NO: 57) of the shaded region.

The results are shown in FIG. 19D. In both the presence and absence of the ORN, the target CpG island was amplified from the bisulfite-converted genomic DNA, but in the presence ORN_hCDKN2A_U, amplification of the target CpG island was reduced. Next, the PCR product obtained in the absence of ORN_hCDKN2A_U and the PCR product obtained in the presence of ORN_hCDKN2A_U were subjected to sequencing. In the case where the nucleotide sequence of the underlined region in FIG. 19B contained methylated cytosines, a signal corresponding to the nucleotide sequence after bisulfite conversion (CG-GATCGCGTGCGTTCGGCGG: SEQ ID NO: 58) is shown in FIG. 19E. In the PCR product obtained in the absence of the ORN, signals corresponding to methylated cytosines and unmethylated cytosines in the CpG sites were detected, but in the PCR product obtained in the presence of ORN_hCDKN2A_U, only signals corresponding to methylated cytosines were detected. These results show that ORN_hCDKN2A_U inhibits DNA amplification from a DNA region having no methylated cytosines in CpG sites of the CpG island in the CDKN2A(p16) locus, but does not affect DNA amplification from a DNA region having methylated cytosines.

To summarize the above, the detection method of the present invention can specifically amplify (enrich) the nucleotide sequence of a DNA region having methylated cytosines in CpG sites (or having no methylated cytosines in CpG sites) after bisulfite conversion. The detection method of the present invention enables more efficient analysis of the methylation pattern of CpG sites in the target DNA region.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for detecting a variation of a reference sequence in a target nucleic acid region,
  wherein the target nucleic acid region in a nucleic acid to be examined for a variation of the reference sequence has sequences identical to upstream and downstream sequences of the reference sequence of a nucleic acid having the reference sequence,
  the method comprising the steps of:
  performing a template-dependent nucleic acid amplification reaction for amplifying a region containing the reference sequence in the target nucleic acid region using, as a template, the nucleic acid to be examined for a variation of the reference sequence, in the presence of a 10 to 200 nucleotide single-stranded nucleic acid capable of hybridizing with the reference sequence, and
  examining the presence or absence of an amplified product,
  wherein the single-stranded nucleic acid is RNA or a chimeric nucleic acid composed of RNA and one or more different nucleic acids,
  wherein the single-stranded nucleic acid contains a sequence complementary to the reference sequence, and
  wherein the single-stranded nucleic acid has a higher complementarity to the reference sequence than to a variant sequence having a variation of the reference sequence and wherein when the target region has no variation of the reference sequence no amplified product is produced because the single stranded nucleic acid hybridizes with the template and inhibits amplification.

2. The detection method according to claim 1, wherein the target nucleic acid region in the nucleic acid having the reference sequence shares the same locus as the target nucleic acid region in the nucleic acid to be examined for a variation of the reference sequence.

3. The detection method according to claim 1, wherein the single-stranded nucleic acid has a complementarity of 100% to the reference sequence.

4. The detection method according to claim 1, wherein the variation of the reference sequence is deletion mutation, insertion mutation, or substitution mutation in the reference sequence, or methylation of a base in the reference sequence.

5. The detection method according to claim 1, wherein the template-dependent nucleic acid amplification reaction is any one selected from the group consisting of PCR, RT-PCR, LAMP, ICAN, NASBA, LCR, SDA, TRC method, TMA, and RPA.

6. The detection method according to claim 5, wherein the template-dependent nucleic acid amplification reaction is PCR.

7. The detection method according to claim 6, wherein the PCR contains a denaturation step, an annealing step, and an elongation step in a cycle.

8. The detection method according to claim 7, wherein the annealing step and the elongation step are performed at the same temperature.

9. The detection method according to claim 1, wherein the single-stranded nucleic acid is 15 to 30 nucleotides in length.

10. The detection method according to claim 1, wherein the single-stranded nucleic acid is a single-stranded RNA.

11. The detection method according to claim 1, wherein the nucleic acid containing the target nucleic acid region is a nucleic acid obtained from a clinical sample of a subject.

12. A method for screening for a cell having a variation of a reference sequence in a target nucleic acid region, the method comprising the steps of:
  preparing a nucleic acid from a subject cell;
  carrying out the detection method according to claim 1 using the obtained nucleic acid as a template and determining the presence or absence of an amplified product; and
  identifying the cell as having a variation of the reference sequence when the presence of the amplified product has been determined.

13. A kit for use in the detection method according to claim 1, the kit comprising a single-stranded nucleic acid, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region.

14. A detection reagent for use in the detection method according to claim 1, the detection reagent comprising a single-stranded nucleic acid, wherein the single-stranded nucleic acid is RNA or a chimeric nucleic acid composed of RNA and one or more different nucleic acids, and wherein the single-stranded nucleic acid contains a sequence complementary to a reference sequence in a target nucleic acid region.

* * * * *